US012674130B2

(12) United States Patent
Huang et al.

(10) Patent No.: US 12,674,130 B2
(45) Date of Patent: Jul. 7, 2026

(54) CLUSTER AIRLIFT BIOREACTOR

(71) Applicant: Ark Biotech Inc., Westwood, MA (US)

(72) Inventors: Zheng Huang, Bolton, MA (US); Kai Hoeffner, Medway, MA (US); Orianna Elysse Kane, Boston, MA (US)

(73) Assignee: Ark Biotech Inc., Westwood, MA (US)

( * ) Notice: Subject to any disclaimer, the term of this patent is extended or adjusted under 35 U.S.C. 154(b) by 416 days.

(21) Appl. No.: 18/525,422

(22) Filed: Nov. 30, 2023

(65) Prior Publication Data

US 2024/0174963 A1 May 30, 2024

Related U.S. Application Data

(63) Continuation-in-part of application No. 18/126,289, filed on Mar. 24, 2023, now Pat. No. 11,884,909.

(60) Provisional application No. 63/334,423, filed on Apr. 25, 2022, provisional application No. 63/334,419, filed on Apr. 25, 2022.

(51) Int. Cl.
*C12M 1/00* (2006.01)
*C12M 1/34* (2006.01)

(52) U.S. Cl.
CPC ............ *C12M 29/24* (2013.01); *C12M 29/06* (2013.01); *C12M 41/26* (2013.01); *C12M 41/34* (2013.01)

(58) Field of Classification Search
CPC ...... C12M 29/24; C12M 29/06; C12M 41/26; C12M 41/34
See application file for complete search history.

(56) References Cited

U.S. PATENT DOCUMENTS

| | | | |
|---|---|---|---|
| 4,183,787 | A | 1/1980 | Roesler |
| 4,782,024 | A | 11/1988 | Scott |
| 5,985,652 | A | 11/1999 | Cheng |
| 9,593,300 | B2 | 3/2017 | Kodukula |
| 10,501,714 | B2 | 12/2019 | Silverman |

(Continued)

FOREIGN PATENT DOCUMENTS

| | | |
|---|---|---|
| CA | 3152432 | 4/2021 |
| CN | 103255046 | 6/2014 |

(Continued)

OTHER PUBLICATIONS

Machine Translation of JP H0716397 B2 (Year: 2026).*

(Continued)

*Primary Examiner* — Michael L Hobbs
(74) *Attorney, Agent, or Firm* — Van Pelt, Yi & James LLP

(57) ABSTRACT

A bioreactor includes one or more sensors, a plurality of spargers, a plurality of vertical circulation loops, and a controller coupled to the plurality of spargers and the one or more sensors. The controller is configured to determine that a reading associated with the bioreactor is not at a setpoint, adjust a sparging rate associated with at least one of the plurality of spargers responsive to gas sparging or a liquid additive being introduced to the bioreactor, wherein the sparging rate associated with the at least one of the plurality of spargers is adjusted from a first sparging rate to a second sparging rate, and in response to the reading associated with the bioreactor being consistent and at the setpoint, modify the sparging rate associated with the at least one of the plurality of spargers from the second sparging rate to the first sparging rate.

22 Claims, 22 Drawing Sheets

(56)                References Cited

U.S. PATENT DOCUMENTS

| | | |
|---|---|---|
| 2005/0260553 A1 | 11/2005 | Berzin |
| 2006/0282225 A1 | 12/2006 | Sunshine |
| 2011/0151507 A1 | 6/2011 | Van Walsem |
| 2012/0305495 A1 | 12/2012 | Siami |
| 2012/0311126 A1 | 12/2012 | Jadallah |
| 2014/0321311 A1 | 10/2014 | Groenendijk |
| 2015/0031099 A1* | 1/2015 | Li .............................. C12P 7/54 |
| | | 435/293.1 |
| 2016/0164761 A1 | 6/2016 | Sathyanarayana |
| 2017/0223036 A1 | 8/2017 | Muddu |
| 2017/0326507 A1 | 11/2017 | Oldani |
| 2018/0119083 A1 | 5/2018 | Zheng |
| 2018/0185794 A1 | 7/2018 | Oldani |
| 2019/0078045 A1 | 3/2019 | Khan |
| 2019/0300838 A1 | 10/2019 | Smith |
| 2019/0345427 A1 | 11/2019 | Bashan |
| 2021/0079334 A1 | 3/2021 | Crater |
| 2022/0042942 A1 | 2/2022 | Hoeffner |
| 2024/0101950 A1 | 3/2024 | Schulz |

FOREIGN PATENT DOCUMENTS

| | | | | |
|---|---|---|---|---|
| CN | 104195033 | 12/2014 | | |
| CN | 105462807 | 4/2016 | | |
| GB | 1356860 | 6/1974 | | |
| JP | H0716397 | 3/1995 | | |
| JP | H0716397 B2 * | 3/1995 | ........... | C12M 29/08 |
| WO | 2007011343 | 1/2007 | | |
| WO | 2016162774 | 10/2016 | | |

OTHER PUBLICATIONS

Han et al., Effect of Aeration Mode on the Performance of Center- and Annulus-Rising Internal-Loop Airlift Bioreactors, Jan. 2018, Can. J. Chem. Eng. 96:367-376 (Year: 2018).

Sanjari et al., "Hydrodynamics and mass transfer coefficients of airlift reactors with net draft tubes of different sizes: Production of cyclodextrin glucanotransferase using *Bacillus* sp." DSM 2523, 2014, Starch, 66, pp. 935-946 (Year: 2014).

* cited by examiner

100

105 exhaust

101

106

102

103

104 air

250

205

252

209

300

400

402

Adjust A Sparging Rate Associated With A Plurality Of Spargers

404

Monitor A Dissolved Oxygen Value Associated With The At Least One Of The Plurality Of Spargers

406

No

Expected Mass Transfer Rate ?

Yes

408

Maintain The Sparging Rate Associated With The Plurality Of Spargers Until A Cell Culture Batch Is Finished

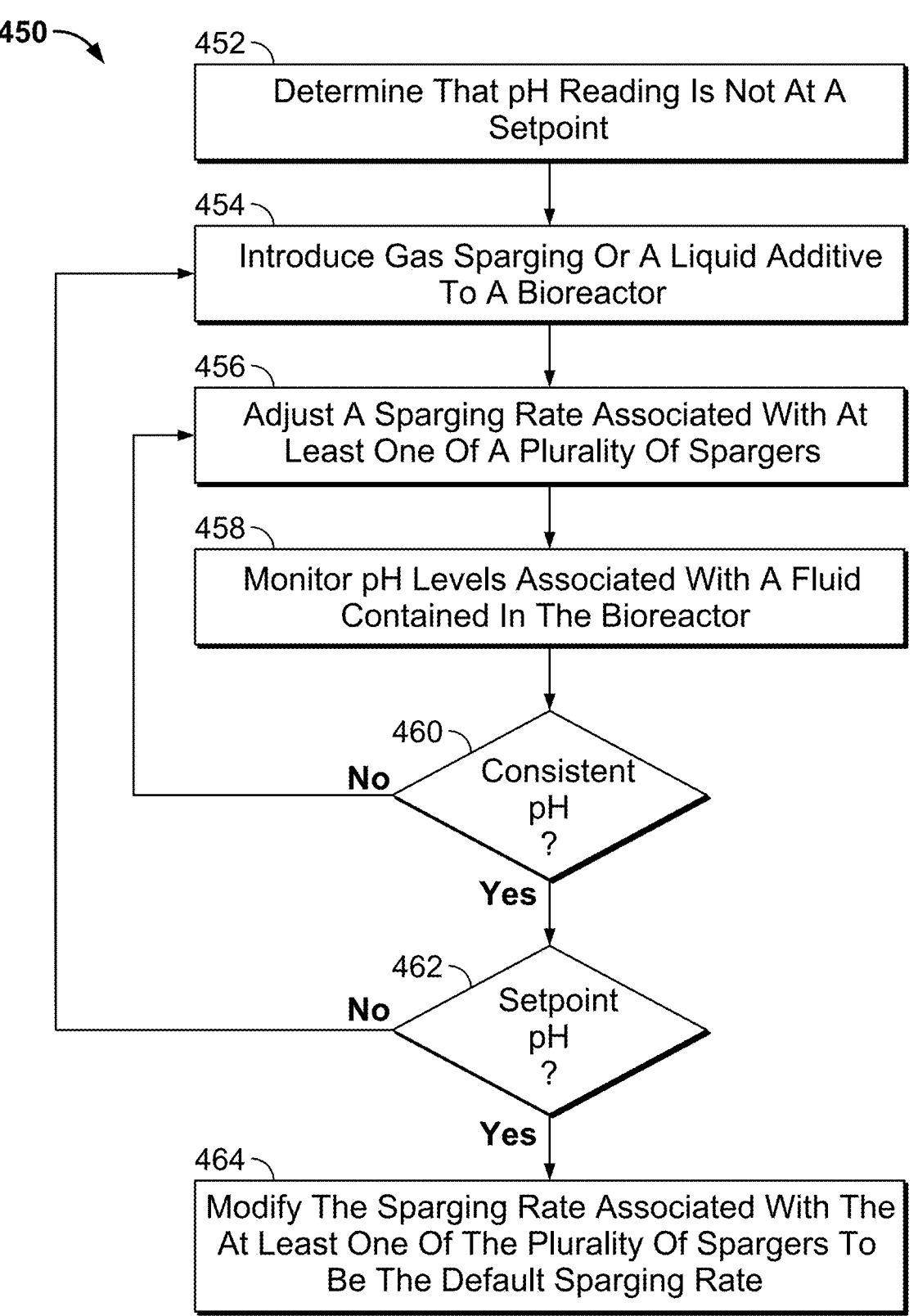

450

452
Determine That pH Reading Is Not At A Setpoint

454
Introduce Gas Sparging Or A Liquid Additive To A Bioreactor

456
Adjust A Sparging Rate Associated With At Least One Of A Plurality Of Spargers 458
Monitor pH Levels Associated With A Fluid Contained In The Bioreactor 460
Consistent pH ?
No
Yes 462
Setpoint pH ?
No
Yes 464
Modify The Sparging Rate Associated With The At Least One Of The Plurality Of Spargers To Be The Default Sparging Rate

612    614a    615a
614b    615b
302
Controller    614c    615c
614d    615d

600

612    615
302
Controller

700

700

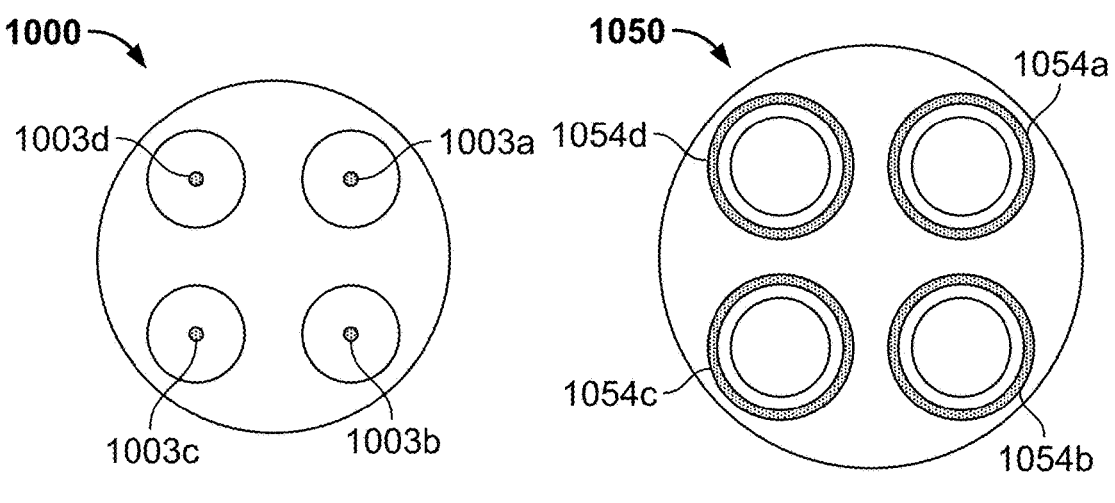
FIG. 10A
FIG. 10C
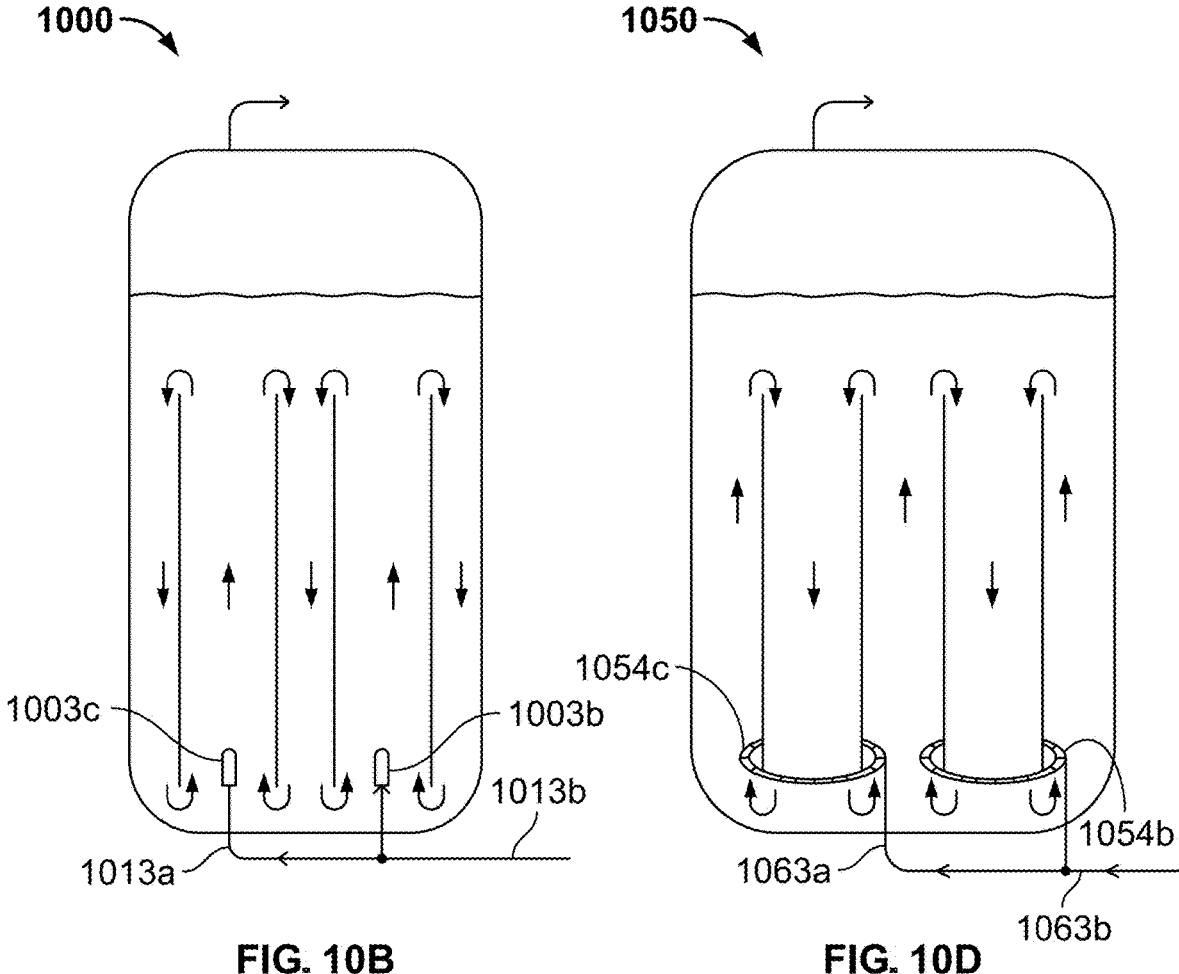
FIG. 10B
FIG. 10D

1100

1600

1700

1702 — Adjust A Sparging Rate Associated With At Least One Of The Spargers Included In the Dual-Sparger Airlift Bioreactor 1704 — Monitor A Dissolved Oxygen Value 1706 — Expected Mass Transfer Rate ?

No

Yes

1708 — Maintain The Sparging Rate Associated With The At Least One Of The Plurality Of Spargers Until A Cell Culture Batch Is Finished

CLUSTER AIRLIFT BIOREACTOR

CROSS REFERENCE TO OTHER APPLICATIONS

This application is a continuation in part of U.S. patent application Ser. No. 18/126,289 entitled CLUSTER AIR-LIFT BIOREACTOR filed Mar. 24, 2023, now U.S. Pat. No. 11,884,909, which claims priority to U.S. Provisional Patent Application No. 63/334,419 entitled CLUSTER BIOREAC-TOR filed Apr. 25, 2022 and to U.S. Provisional Patent Application No. 63/334,423 entitled AIRLIFTING BIORE-ACTOR filed Apr. 25, 2022, each of which is incorporated herein by reference for all purposes.

BACKGROUND OF THE INVENTION

As the size of a stirred tank bioreactor increases, the mixing of the liquid in the bioreactor becomes increasingly difficult with a single agitator. As a result, it is difficult to provide an ideal environment for cell culture to grow. It is also more challenging to supply oxygen to cells and sweep dissolved carbon dioxide ($dCO_2$), a metabolic waste produced by cells. Greater sparging demand is required. By reducing the bubble size, it is possible to reduce sparging demand, but smaller bubbles exert more damage to cells than bigger ones and exacerbate the foaming problem. Most conventional measures to adapt cell culture to a bigger stirred tank bioreactor end up hurting cells or increasing the cost, thus making scaling-up bioreactor a challenging task, and limiting how the scalability of a bioreactor.

Airlift bioreactors are commonly used in microbial fermentation. Under the protection of a sturdy cell wall, microbes can withstand very high sparging rates and achieve fast growth and high culture density. Cells used in cell culture only have cell membranes to protect them and could not take high stress from excessive sparging. To achieve high cell density, it is critical to minimize sparging while still meeting the mass transfer and mixing requirements.

Airlifting design is known to have intrinsically low mechanic shear and turbulence, which is beneficial to cell heath. However, to increase cell density, a greater amount of sparging air is needed to supply oxygen and sweep dissolved carbon dioxide. Similar to a stirred tank design, the gas sparging in an airlift bioreactor negatively affects cell health. When cell density increases, the high sparging demand could impede cell growth or become detrimental to cell health, setting a ceiling on how high a cell density can go in an airlift bioreactor.

Furthermore, the performance of an airlift bioreactor is largely determined by the geometry and aspect ratio of its dimensions. The ratio of the cross-sectional area between the tube included in the airlift bioreactor and annulus of the airlift bioreactor, as well as the diameter-to-height ratio of the tube, are two key design parameters that can impact the efficiency of the airlift bioreactor.

The volume of the airlift bioreactor that is used as the riser or downcomer depends on the mode of operation, which can be either annular or tube sparged. The riser is typically the volume that is predominantly sparged (e.g., sparging region), while the downcomer is usually the volume that is not sparged or is sparged to a lesser extent (e.g., return region). Mixing time and mass transfer in an airlift biore-actor are primarily influenced by the difference in gas holdup between the riser and downcomer. A difference in gas holdup between the two volumes creates a difference in density that generates a driving force for liquid movement proportional to the difference. The liquid recirculation velocity in the riser and downcomer affects overall mixing and mass transfer characteristics of an airlift bioreactor.

FIG. 1 illustrates an example of an airlift bioreactor. The airlift bioreactor 100 includes a vessel 101 having a tall cylindrical shape and an inner tube 102. Gas 104, such as air, may be sparged inside the inner tube 102 via sparger 103. The gas-liquid mixture in the inner tube 102 is lighter than the liquid in the annulus space, causing the liquid 106 to form a recirculating loop between the inner tube 102 and the annular space. The recirculating flow effectively mixes the bioreactor 100, thus eliminating the need for an agitator and greatly reducing the cost and risk of contamination. Air may supply oxygen to cells, while dissolved carbon dioxide ($dCO_2$), a metabolic waste produced by cells, may be swept away via exhaust 105.

BRIEF DESCRIPTION OF THE DRAWINGS

Various embodiments of the invention are disclosed in the following detailed description and the accompanying drawings.

FIG. 4B is a flow diagram illustrating a process for operating a cluster airlift bioreactor in accordance with some embodiments.

FIG. 10A depicts a top-down view of a cluster airlift bioreactor in accordance with some embodiments.

FIG. 10B depicts a side view of a cluster airlift bioreactor in accordance with some embodiments.

FIG. 10C depicts a top-down view of a cluster airlift bioreactor in accordance with some embodiments.

FIG. 10D depicts a side view of a cluster airlift bioreactor in accordance with some embodiments.

DETAILED DESCRIPTION

Figure 1:
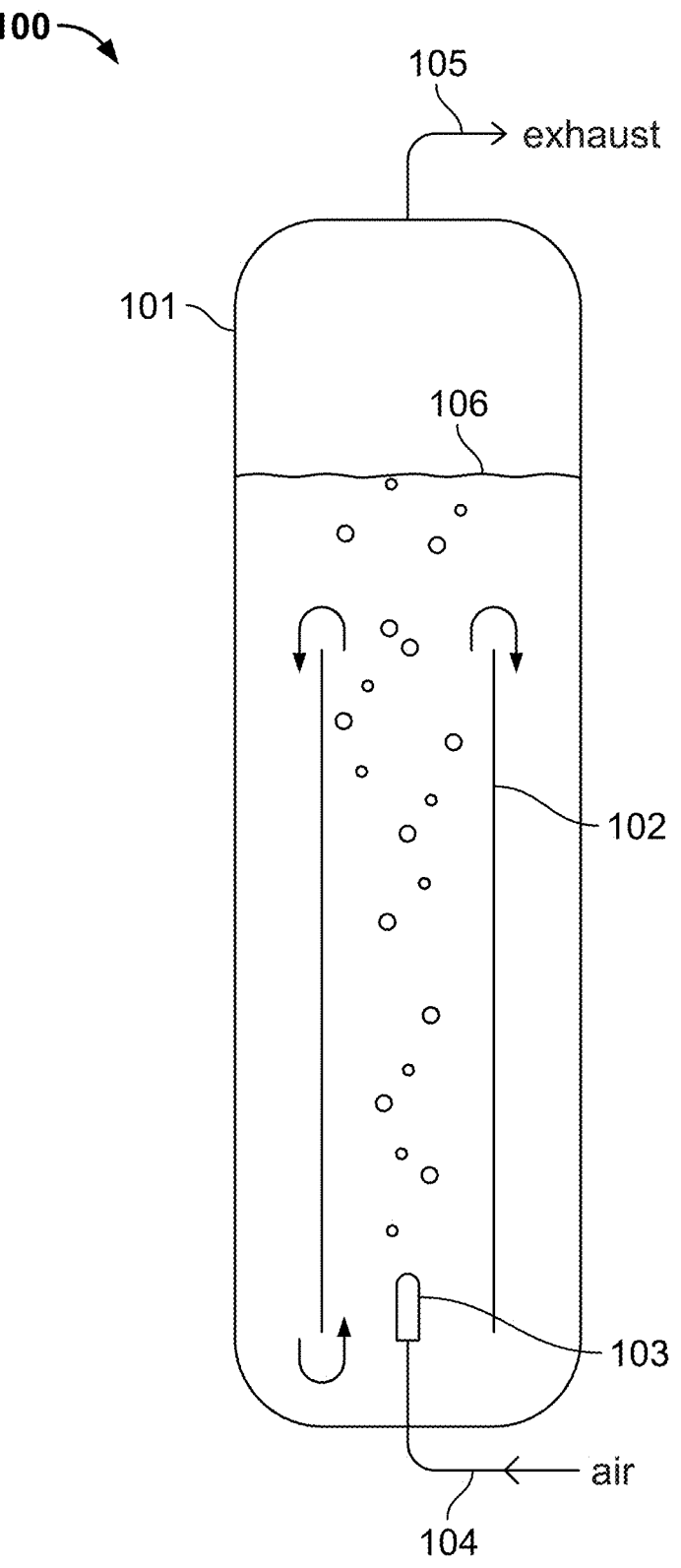
FIG. 1 illustrates an example of an airlift bioreactor.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Airlift bioreactors avoid the complications associated with a large agitator in stirred tank bioreactors and provide an attractive solution to cell culture scale up. An airlift bioreactor may be designed to have a particular performance (e.g., mass transfer coefficient, shear turbulence, mixing, etc.). The airlift bioreactor may be scaled up by increasing a size of a vessel associated with the airlift bioreactor, however, increasing the size of the vessel may change the performance of the airlift bioreactor. The particular performance of the airlift bioreactor may be maintained to a certain degree by maintaining a height-to-diameter ratio of the tube of the airlift bioreactor and cross-sectional area ratio between the tube and annulus of the airlift bioreactor constant as the size of the airlift bioreactor increases. However, one limitation with this approach is that there is an upper limit to which the airlift bioreactor may be scaled up due to the physical dimensions of a building housing the airlift bioreactor. A maximum height of a building may be reached (e.g., the height of the ceiling), which prohibits further increase in airlift bioreactor volume without impacting the airlift bioreactor performance.

A cluster airlift bioreactor is disclosed herein. The cluster airlift bioreactor increases a cross-sectional area of the vessel associated with an airlift bioreactor and adds a plurality of tubes within the vessel. The performance of a single airlift bioreactor may be scaled up using the cluster airlift bioreactor. The performance of the single airlift bioreactor is based on height-to-diameter ratio of the tube of the airlift bioreactor and cross-sectional area ratio between the tube and annulus of the airlift bioreactor constant. The single airlift bioreactor may be scaled up and the performance associated with the single airlift bioreactor may be maintained by the cluster airlift bioreactor within a threshold by maintaining the tube height-to-diameter ratio of the single airlift bioreactor and applying the same ratio to all tubes included in the cluster airlift bioreactor and maintaining a ratio of the cross-sectional area of the sum of all tubes over the cross-section area of the annulus region of the vessel (e.g., the area between the walls of the vessel and the tubes) to match the cross-sectional area ratio between the tube and annulus of the single airlift bioreactor. The cluster airlift bioreactor may be used to cultivate meat production of mammalian, avian, fish, reptile, crustacean, or mollusca cell mass for human or animal consumption. The cluster airlift bioreactor may be used to cultivate non-tissue body parts of animal for making consumer goods (e.g., leather). The cluster airlift bioreactor may be used for cellular agriculture of plant cells to replace conventional production. The cluster airlift bioreactor may be used for biopharmaceutical culture of rodent, primate, and insect cells for the production of cell therapy, gene therapy, antibody, nanobody, enzyme, fusion protein, implant, and vaccine. The cluster airlift bioreactor may be used for culture of bacteria, algae, and fungus for the production of commodity food/feed/biofuel ingredients.

Figures 2A, 2B:
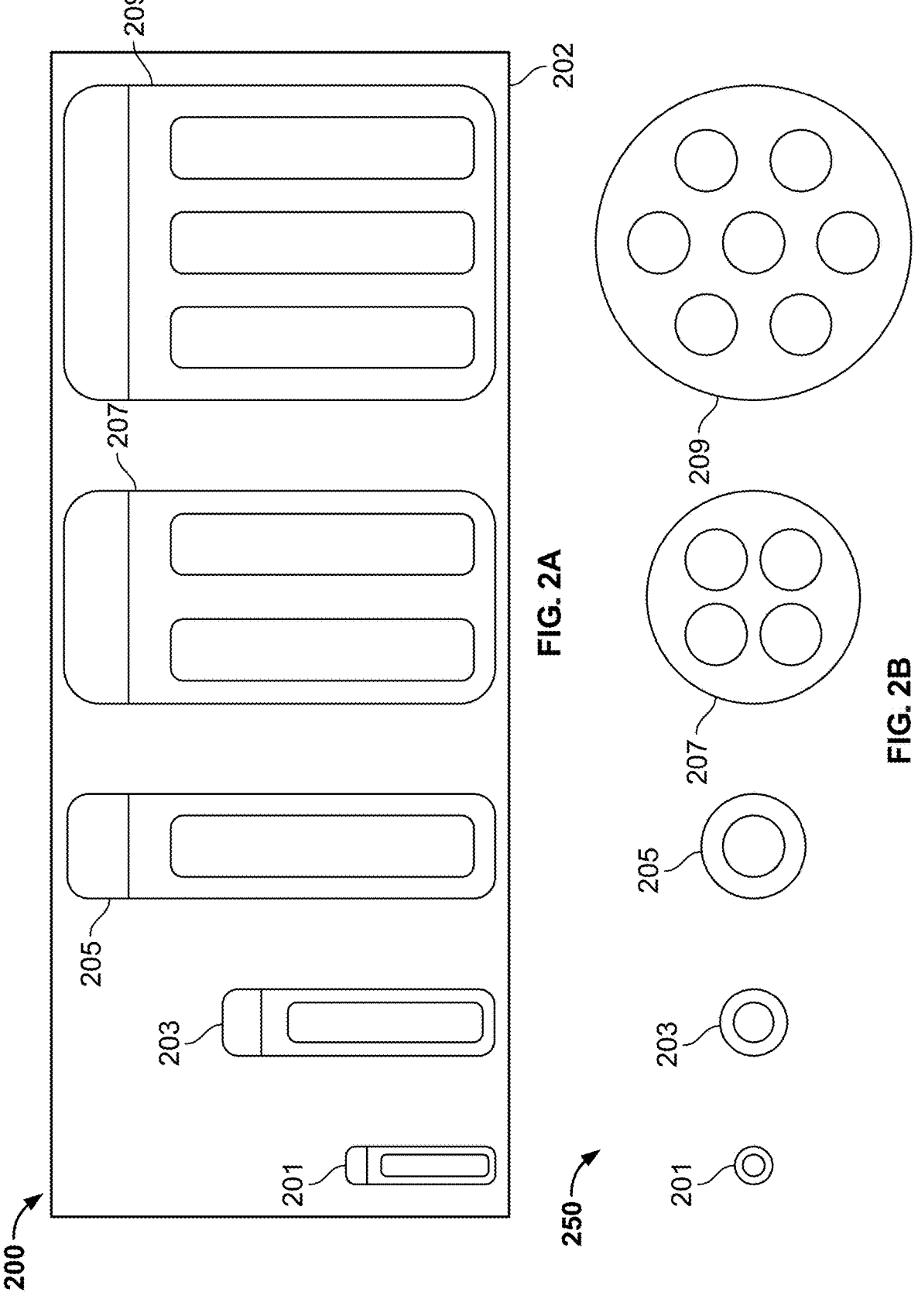
FIG. 2A is a side view of a plurality of airlift bioreactors in accordance with some embodiments.
FIG. 2B is a top-down view of a plurality of airlift bioreactors in accordance with some embodiments.

FIG. 2A is a side view 200 of a plurality of airlift bioreactors in accordance with some embodiments. FIG. 2B is a top-down view 250 of the plurality of airlift bioreactors in accordance with some embodiments. In the example shown, airlift bioreactors 201, 203, 205, 207, 209 are housed within building 202. Airlift bioreactor 201 may be scaled up by increasing a size of a vessel associated with airlift bioreactor 201. The particular performance of airlift bioreactor 201 may be maintained by maintaining a height-to-diameter ratio of the tube and cross-sectional area ratio between the tube and annulus constant as airlift bioreactor

201 increases in size to become airlift bioreactor 203 or airlift bioreactor 205. There is an upper limit to which airlift bioreactor 201 may be scaled up by merely increasing the size of the vessel due to the physical dimensions of building 202. As seen in FIG. 2A, the height of airlift bioreactor 205 has reached the height of building 202.

Figure 2C:
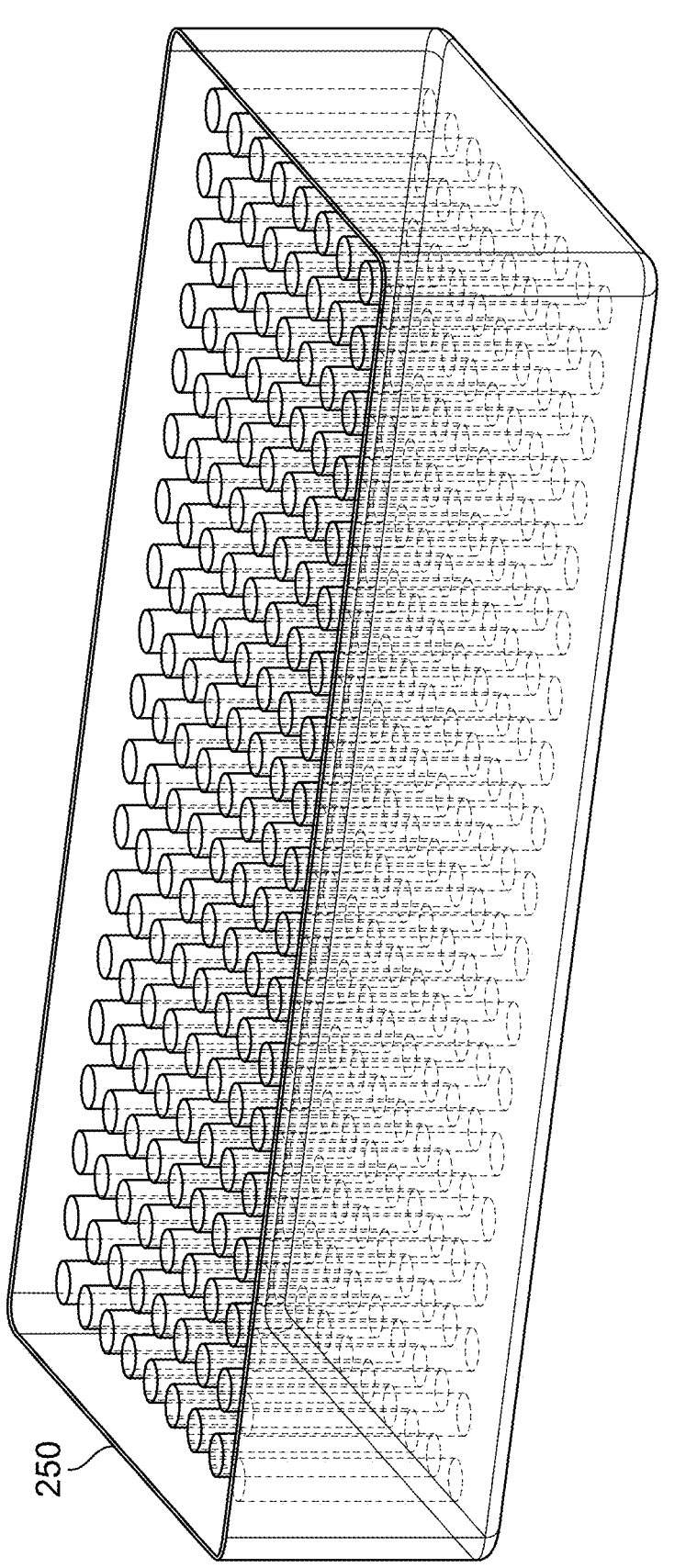
FIG. 2C is an example of a plurality of airlift tubes being housed within a vessel in accordance with some embodiments.
Figure 2D:
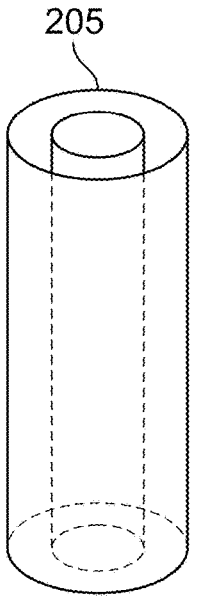
FIG. 2D depicts an airlift bioreactor being scaled up in accordance with some embodiments.
Figure 2D:
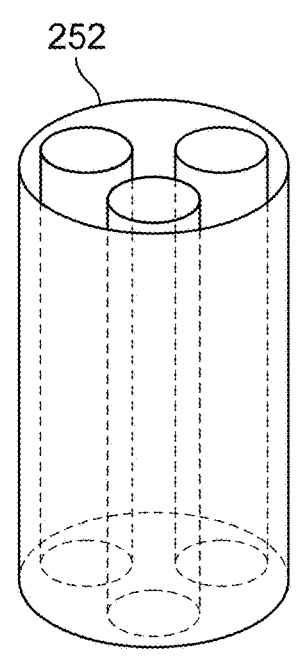
Figure 2D:
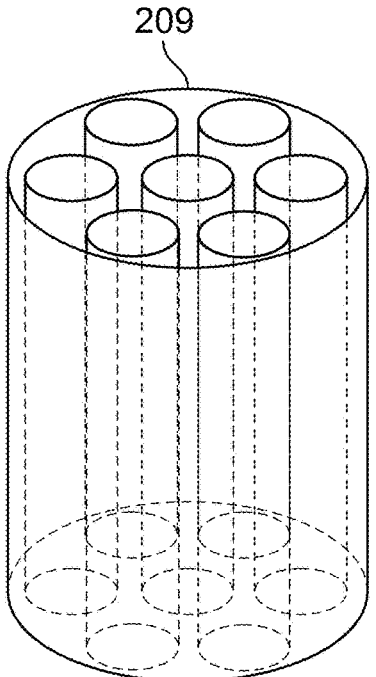

Airlift bioreactor 205 may be further scaled up by increasing a cross-sectional area of the vessel and adding a plurality of airlift tubes within the vessel. As seen in FIGS. 2A and 2B, airlift bioreactor 207 has increased the volume of the vessel associated with airlift bioreactor 205 and added three additional tubes. Airlift bioreactor 209 has increased the volume of the vessel associated with airlift bioreactor 205 and added six additional tubes. Although FIGS. 2A and 2B depict airlift bioreactor 205 being scaled up to include 4 and 7 tubes, airlift bioreactor 105 may be scaled up to include n tubes (e.g., between 3-400 tubes). FIG. 2D depicts airlift bioreactor 205 being scaled up to become air reactor 252 (3 tubes) and airlift bioreactor 209 (7 tubes). Airlift bioreactor 205 may be scaled up and the performance associated with airlift bioreactor 205 may be maintained within a threshold by maintaining the height-to-diameter ratio of an individual tube associated with airlift bioreactor 205 across all tubes of the cluster airlift bioreactor and maintaining the ratio of the cross-sectional area of the sum of all tubes over the cross-section area of the annulus region of the vessel to match the cross-sectional area ratio between the tube and annulus of airlift bioreactor 105. An example of this is shown in FIG. 2C, which depicts a plurality of tubes being housed within a vessel 250. In some embodiments, the bottom of vessel 250 is flat. In some embodiments, the bottom of vessel 250 includes a plurality of concave holdings for the plurality of tubes to facilitate solid suspension of the plurality of tubes. In some embodiments, there are physical baffles between adjacent airlift modules to reduce lateral fluid movement and enforce vertical flow field. The baffles may impose partial or full restriction of liquid movement between modules. In some embodiments, the physical baffles are fins that are located on an inside wall of vessel 250. In some embodiments, the physical baffles are fins that are located on the airlift tubes.

Figure 2E:
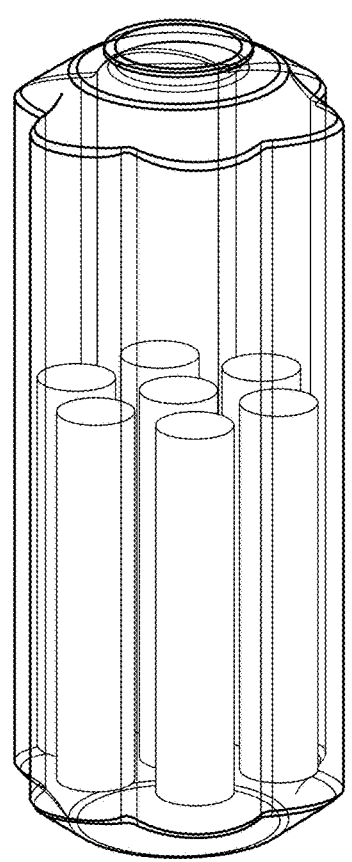
FIG. 2E depicts an example of a vessel associated with an airlift bioreactor in accordance with some embodiments.

The vessel associated with an airlift bioreactor may have a cylindrical shape, a rectangular shape, a triangular shape, a square shape, a pentagon shape, a hexagon shape, a heptagon shape, an octagon shape, a nonagon shape, a decagon shape, or any other shape. FIG. 2D depicts the vessel associated with an airlift bioreactor having a cylindrical shape. FIG. 2E depicts the vessel associated with an airlift bioreactor having a hexagon shape. The shape of the vessel may be selected to better fit the tubes associated with the airlift bioreactor or better fit the surrounding of installation location.

An airlift tube may have a cylindrical shape, a rectangular shape, a triangular shape, a square shape, a pentagon shape, a hexagon shape, a heptagon shape, an octagon shape, a nonagon shape, a decagon shape, or any other shape. The shapes of the airlift tubes within the vessel may be different. For example, the airlift tubes near the wall of the vessel and those in the center may have different shapes.

Figure 3:
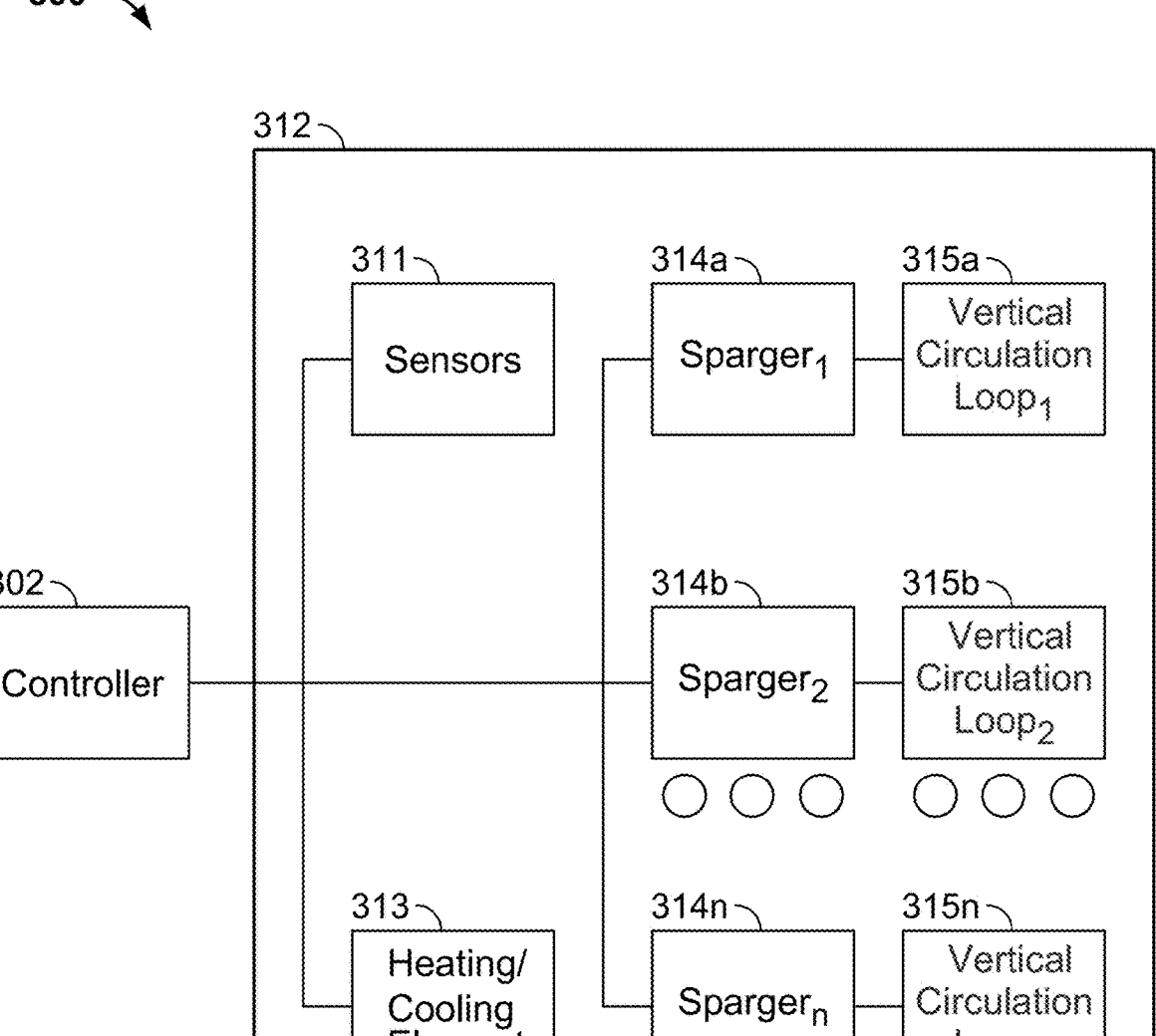
FIG. 3 is a block diagram illustrating a cluster airlift bioreactor in accordance with some embodiments.

FIG. 3 is a block diagram illustrating a cluster airlift bioreactor in accordance with some embodiments. In the example shown, cluster airlift bioreactor 300 includes a controller 302 coupled to a vessel 312. Vessel 312 includes one or more sensors 311, a heating/cooling element 313, and a plurality of spargers 314a, 314b, . . . , 314n associated with a plurality of vertical circulation loops 315a, 315b, . . . , 315n. In some embodiments, a vertical circulation loop includes a riser portion (e.g., sparging region) and a downcomer portion (e.g., return region). For example, the area within the tube 102 of airlift bioreactor 100 may correspond to the riser portion of the vertical circulation loop and the annulus area of airlift bioreactor 100 may correspond to the downcomer portion of the vertical circulation loop. In some embodiments, the riser portion of the vertical circulation loop is internal to vessel 312 and the downcomer portion of the vertical circulation loop is external to vessel 312. In some embodiments, the riser portion of the vertical circulation loop is external to vessel 312 and the downcomer portion of the vertical circulation loop is internal to vessel 312.

Although FIG. 3 depicts vessel 312 including three spargers and three vertical circulation loops, cluster airlift bioreactor 300 may include n spargers with n vertical circulation loops. Controller 302 is configured to increase or decrease a corresponding sparging rate associated with the plurality of spargers 314a, 314b, . . . , 314n.

An individual vertical circulation loop is characterized by an individual loop mass transfer coefficient, mixing time, recirculation flow rate, and bubble residence time. Controller 302 is configured to control the plurality of spargers 314a, 314b, . . . , 314n together such that a cumulative mass transfer coefficient of the plurality of vertical circulation loops is within a threshold of the individual loop mass transfer coefficient associated with the individual vertical circulation loop. Controller 302 is configured to control the plurality of spargers 314a, 314b, . . . , 314n together such that a cumulative mixing time of the plurality of vertical circulation loops is within a threshold of the individual mixing associated with the individual vertical circulation loop. Controller 302 is configured to control the plurality of spargers 314a, 314b, . . . , 314n together such that a cumulative recirculation flow rate of the plurality of vertical circulation loops is within a threshold of the individual recirculation flow rate associated with the individual vertical circulation loop. Controller 302 is configured to control the plurality of spargers 314a, 314b, . . . , 314n together such that a cumulative bubble residence time of the plurality of vertical circulation loops is within a threshold of the individual bubble residence time associated with the individual vertical circulation loop.

In some embodiments, the controller 302 controls the sparging rate associated with the plurality of spargers 314a, 314b, . . . , 314n to be the same sparging rate. This causes vertical mixing to occur within the plurality of vertical circulation loops 315a, 315b, . . . , 315n. Some horizontal mixing may occur between the vertical circulation loops 315a, 315b, . . . , 315n when the sparging rate associated with the plurality of spargers 314a, 314b, . . . , 314n is the same, however, the predominant form of mixing in this embodiment is vertical mixing.

In some embodiments, the controller 302 controls the sparging rate associated with at least one of the plurality of spargers 314a, 314b, . . . , 314n to be different than the other spargers. This causes horizontal mixing to occur within the plurality of vertical circulation loops 315a, 315b, . . . , 315n. When an additive is introduced to the cluster airlift bioreactor, horizontal mixing may be desired to increase the speed at which and reduce the amount of time needed to diffuse the additive throughout the entire working volume of the cluster airlift bioreactor.

The one or more sensors 311 may include a pH sensor, a temperature sensor, a dissolved oxygen sensor, a dissolved carbon dioxide sensor, a bio-capacitance sensor, a Raman spectroscopy sensor, a near-infrared light sensor, etc.

Heating/cooling element 313 may be used to adjust a temperature of the liquid within vessel 312 to a desired temperature.

Cluster airlift bioreactor 300 may include different configurations of spargers. In some embodiments, all of the spargers 314a, 314b, . . . , 314n included in cluster airlift bioreactor 300 are tube spargers. In some embodiments, all of the spargers 314a, 314b, . . . , 314n included in cluster airlift bioreactor 300 are annulus spargers. In some embodiments, each of the vertical circulation loops 315a, 315b, . . . , 315n are associated with a corresponding tube sparger and a corresponding annulus sparger. In some embodiments, spargers can be straight. In some embodiments, spargers can be curved or a partial ring.

In some embodiments, some of the vertical circulation loops 315a, 315b, . . . , 315n are associated with a corresponding tube sparger, some of the vertical circulation loops 315a, 315b, . . . , 315n are associated with a corresponding annulus sparger, and some of the vertical circulation loops 315a, 315b, . . . , 315n are associated with a corresponding tube sparger and a corresponding annulus sparger.

Figure 4A:
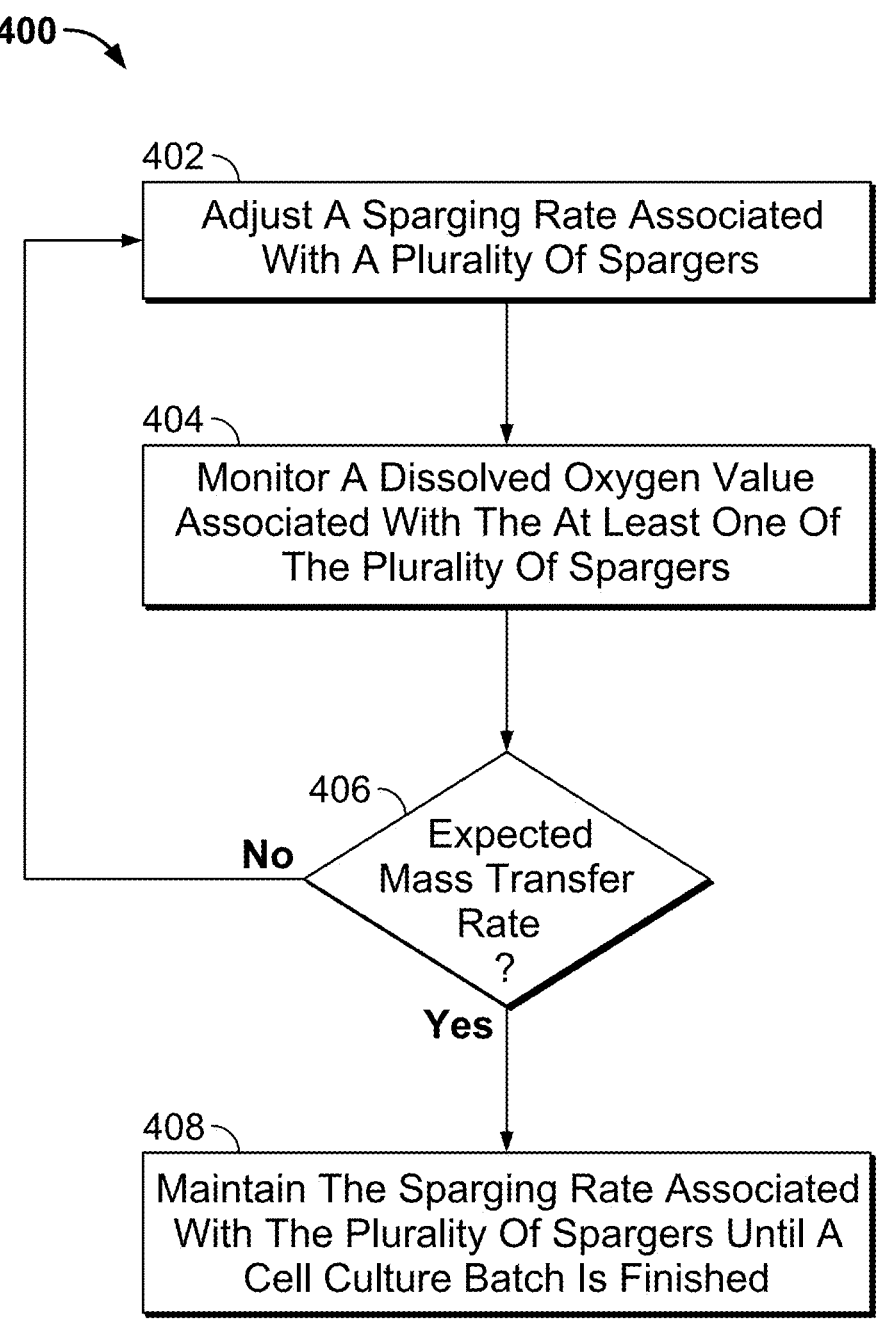
FIG. 4A is a flow diagram illustrating a process for operating a cluster airlift bioreactor in accordance with some embodiments.

FIG. 4A is a flow diagram illustrating a process for operating a cluster airlift bioreactor in accordance with some embodiments. In the example shown, process 400 may be implemented by a controller, such as controller 302.

At 402, a sparging rate associated a plurality of spargers is adjusted to be a same sparging rate. Each of the plurality of spargers is coupled to a controller, which controls the corresponding sparging rate for the plurality of spargers. Sparging enables mixing within the airlift bioreactor to occur, provides oxygen for cells to consume, and sweeps away carbon dioxide waste that cells produce. In some embodiments, a vertical circulation loop is associated with a tube sparger and a sparging rate associated with the tube sparger is adjusted. In some embodiments, a vertical circulation loop is associated with an annulus sparger and a sparging rate associated with the annulus sparger is adjusted. In some embodiments, a vertical circulation loop is associated with a tube sparger and an annulus sparger, and a sparging rate associated with the tube sparger and/or the annulus sparger is adjusted.

At 404, a dissolved oxygen value associated with the plurality of spargers is monitored. The cluster airlift bioreactor is designed in a manner such that a performance of the cluster airlift bioreactor matches a performance of a single airlift bioreactor within a threshold. A performance of an airlift bioreactor may be quantified using a mass transfer coefficient. The mass transfer coefficient is a parameter that determines the rate at which a gaseous compound (e.g., $O_2$ or $CO_2$) can transfer between the gas phase and the liquid phase. The mass transfer coefficient of the cluster airlift bioreactor may be designed to match the mass transfer coefficient of a single airlift bioreactor by maintaining the height-to-diameter ratio of the tube included in the single airlift bioreactor for all tubes included in the cluster airlift bioreactor and maintaining a ratio of the cross-sectional area of the sum of all tubes over the cross-section area of the annulus region of the vessel (e.g., the area between the walls of the vessel and the tubes) to match the cross-sectional area ratio between the tube and annulus of the single airlift bioreactor.

The mass transfer rate associated with the plurality of spargers is calculated in real-time as the plurality of spargers operate. The mass transfer between the gas-liquid interface is well known. The mass transfer behaviors of bubbles rising in liquid can be solved as ordinate differential equations (ODEs). The equivalent mass transfer rate can be calculated from how much oxygen successfully transferred from the gas phase into the liquid phase.

At 406, it is determined whether the monitored mass transfer rate is within a threshold of an expected mass transfer rate. The expected mass transfer rate corresponds to the mass transfer rate associated with a single airlift bioreactor. The cumulative mass transfer rate associated with the plurality of spargers may increase by increasing the sparging rate associated with the plurality of spargers.

In response to a determination that the monitored mass transfer rate is within the threshold of the expected mass transfer rate, process 400 proceeds to 408. In response to a determination that the monitored mass transfer rate is not within the threshold of the expected mass transfer rate after a particular period of time, process 400 returns to step 402.

At 408, the sparging rate associated with the plurality of spargers is maintained until a cell culture batch is finished.

FIG. 4B is a flow diagram illustrating a process for operating a cluster airlift bioreactor in accordance with some embodiments. In the example shown, process 450 may be implemented by a controller, such as controller 302, to control pH.

At 452, it is determined that a pH reading associated with the bioreactor is not at a setpoint. In some embodiments, a pH setpoint associated with the bioreactor is fixed during a cell culture run. In some embodiments, a pH setpoint associated with bioreactor changes during a cell culture run.

At 454, gas sparging or a liquid additive is introduced to the bioreactor. The bioreactor includes a liquid having an associated pH. Introducing an additive or gas sparging can be used to maintain the pH setpoint. The additive may be introduced to the bioreactor to adjust the pH associated with the bioreactor to one direction. In some embodiments, the additive is a base to increase pH. In some embodiments, the additive is an acid to decrease pH. In some embodiments, gas sparging has high nitrogen concentration (e.g., greater than a nitrogen concentration threshold) to increase pH. In some embodiments, gas sparging has high carbon dioxide concentration (e.g., greater than a carbon dioxide threshold) to decrease pH. In some embodiments, the liquid additive is inoculant (e.g., cell culture media associated with a plurality of cells, an acid, a base, a buffering compound, or a nutrient feed.

At 456, a sparging rate associated with at least one of a plurality of spargers is adjusted. The sparging rate associated with at least one of the plurality of spargers is adjusted to be different than one or more other spargers. This causes intentional horizontal mixing to occur within the cluster airlift bioreactor. Horizontal mixing may be desired when the additive needs to be quickly dissipated throughout the cluster airlift bioreactor so that the additive does not remain in a localized area of the cluster airlift bioreactor for an extended period of time.

In some embodiments, a plurality of vertical circulation loops is associated with a corresponding tube sparger and a sparging rate associated with at least one of the tube spargers is adjusted. In some embodiments, a plurality of vertical circulation loops is associated with a corresponding annulus sparger and a sparging rate associated with at least one of the annulus spargers is adjusted. In some embodiments, a plurality of vertical circulation loops is associated with a corresponding tube sparger and a corresponding annulus sparger. The sparging rate associated with both the tube sparger and the annulus sparger of at least one of the plurality of vertical circulation loops is adjusted.

At 458, a pH level associated with a liquid contained in the bioreactor is monitored. The pH level associated with the liquid is monitored for a particular amount of time.

At 460, after the pH level associated with the liquid has been monitored for the particular amount of time, it is determined whether the pH level associated with the liquid is consistent. The bioreactor includes a plurality of pH sensors that are located at different locations throughout the bioreactor. A pH level associated with the liquid that is consistent (e.g., the readings of the pH sensors are equal) indicates that the gas or liquid additive has been evenly distributed throughout the bioreactor. A pH level associated with the liquid that is not consistent indicates that the gas or liquid additive has not been evenly distributed throughout the bioreactor. In response to a determination that the pH level associated with the liquid is consistent, process 450 proceeds to 462. In response to a determination that the pH level associated with the liquid is not consistent, process 450 returns to 456. In some embodiments, in response to a determination that the pH level associated with the liquid is not consistent, process 450 returns to 458.

At 462, it is determined whether the current pH matches the setpoint pH. The liquid is expected to have a particular pH after the additive is added to the bioreactor. The expected pH is established as the setpoint pH. In response to a determination that the pH level associated with the liquid matches the setpoint pH, process 450 proceeds to 464. In response to a determination that the pH level associated with the liquid does not match the setpoint pH, process 450 returns to 454.

At 464, the sparging rate associated with the at least one of the plurality of spargers is modified to be the default sparging rate. The sparging rate associated with the at least one of the plurality of spargers is modified to be the same sparging rate associated with one or more other spargers included in the cluster airlift bioreactor. This changes the mixing state of the cluster airlift bioreactor from horizontal mixing to vertical mixing.

Figure 4C:
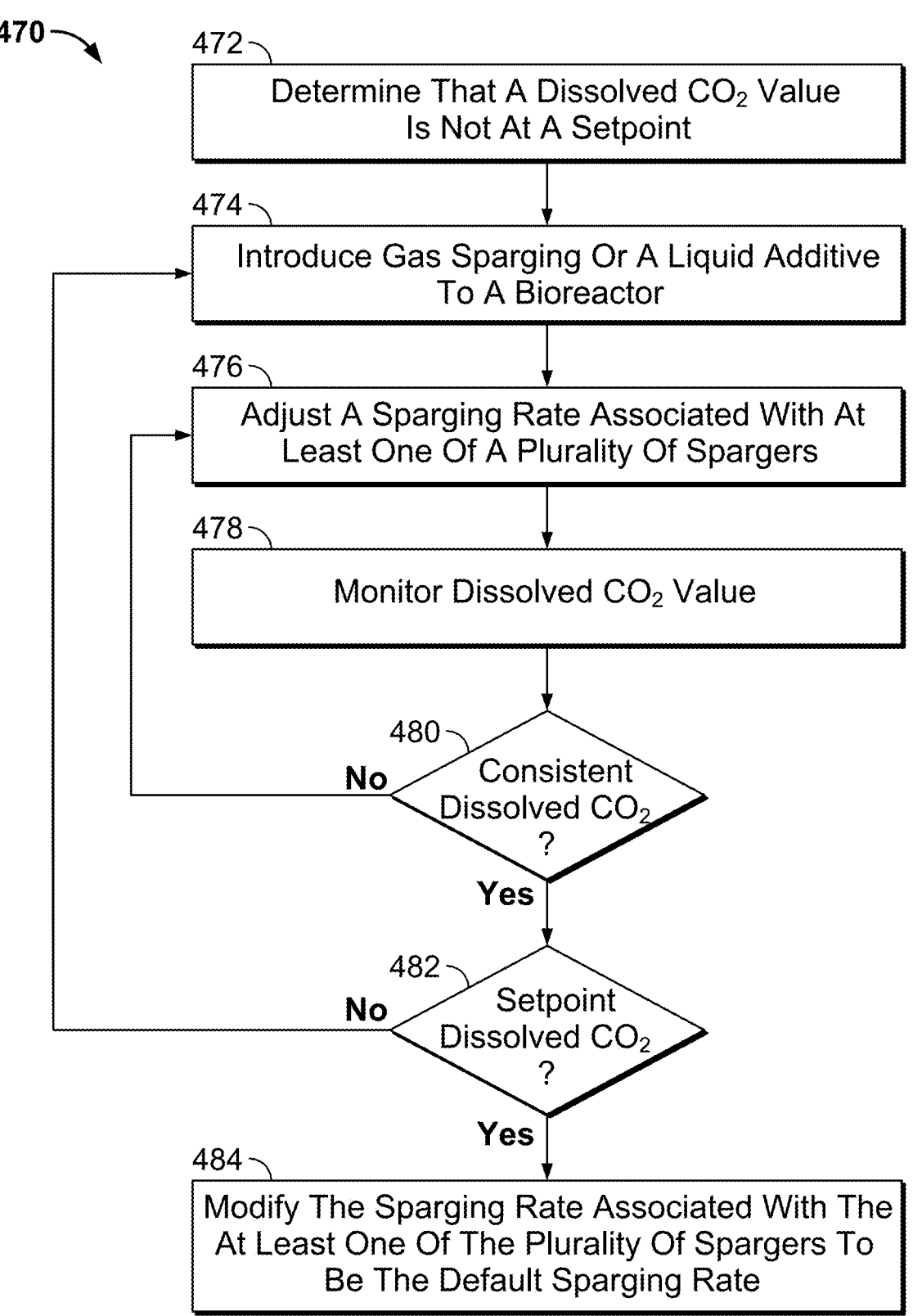
FIG. 4C is a flow diagram illustrating a process for operating a cluster airlift bioreactor in accordance with some embodiments.

FIG. 4C is a flow diagram illustrating a process for operating a cluster airlift bioreactor in accordance with some embodiments. In the example shown, process 450 may be implemented by a controller, such as controller 302, to control dissolved $CO_2$ in a bioreactor.

At 472, it is determined that a dissolved $CO_2$ reading associated with the bioreactor is not at a setpoint. In some embodiments, a dissolved $CO_2$ setpoint associated with the bioreactor is fixed during a cell culture run. In some embodiments, a dissolved $CO_2$ setpoint associated with bioreactor changes during a cell culture run.

At 474, gas sparging or a liquid additive is introduced to the bioreactor. The bioreactor has an associated dissolved $CO_2$ value. Introducing an additive or gas sparging can be used to maintain the dissolved $CO_2$ setpoint. The additive may be introduced to the bioreactor to increase or decrease the dissolved $CO_2$ value. In some embodiments, the liquid additive is sodium bicarbonate or sodium carbonate solution.

At 476, a sparging rate associated with at least one of a plurality of spargers is adjusted. The sparging rate associated with at least one of the plurality of spargers is adjusted to be different than one or more other spargers. This causes intentional horizontal mixing to occur within the cluster airlift bioreactor. Horizontal mixing may be desired when the additive needs to be quickly dissipated throughout the cluster airlift bioreactor so that the additive does not remain in a localized area of the cluster airlift bioreactor for an extended period of time.

In some embodiments, a plurality of vertical circulation loops is associated with a corresponding tube sparger and a sparging rate associated with at least one of the tube spargers is adjusted. In some embodiments, a plurality of vertical circulation loops is associated with a corresponding annulus sparger and a sparging rate associated with at least one of the annulus spargers is adjusted. In some embodiments, a plurality of vertical circulation loops is associated with a corresponding tube sparger and a corresponding annulus sparger. The sparging rate associated with both the tube sparger and the annulus sparger of at least one of the plurality of vertical circulation loops is adjusted.

At 478, the dissolved $CO_2$ readings in the bioreactor are monitored. The dissolved $CO_2$ value is monitored for a particular amount of time.

At 480, after the dissolved $CO_2$ value has been monitored for the particular amount of time, it is determined whether the dissolved $CO_2$ value is consistent. The bioreactor includes one or more dissolved $CO_2$ sensors that are located at different locations throughout the bioreactor. A dissolved $CO_2$ value that is consistent (e.g., the readings of the dissolved $CO_2$ sensors are equal) indicates that the gas or liquid additive has been evenly distributed throughout the bioreactor. A dissolved $CO_2$ value that is not consistent indicates that the gas or liquid additive has not been evenly distributed throughout the bioreactor. In response to a determination that the dissolved $CO_2$ value is consistent, process 470 proceeds to 482. In response to a determination that the dissolved $CO_2$ value is not consistent, process 470 returns to 476. In some embodiments, in response to a determination that the dissolved $CO_2$ value is not consistent, process 470 returns to 478.

At 482, it is determined whether the current dissolved $CO_2$ value matches the setpoint dissolved $CO_2$ value. The liquid is expected to have a particular dissolved $CO_2$ value the additive is added to the bioreactor. The expected dissolved $CO_2$ value is established as the setpoint dissolved $CO_2$ value. In response to a determination that the dissolved $CO_2$ value matches the setpoint dissolved $CO_2$ value, process 470 proceeds to 484. In response to a determination that the dissolved $CO_2$ value does not match the setpoint dissolved $CO_2$ value, process 470 returns to 474.

At 484, the sparging rate associated with the at least one of the plurality of spargers is modified to be the default sparging rate. The sparging rate associated with the at least one of the plurality of spargers is modified to be the same sparging rate associated with one or more other spargers included in the cluster airlift bioreactor. This changes the mixing state of the cluster airlift bioreactor from horizontal mixing to vertical mixing.

Figure 5A:
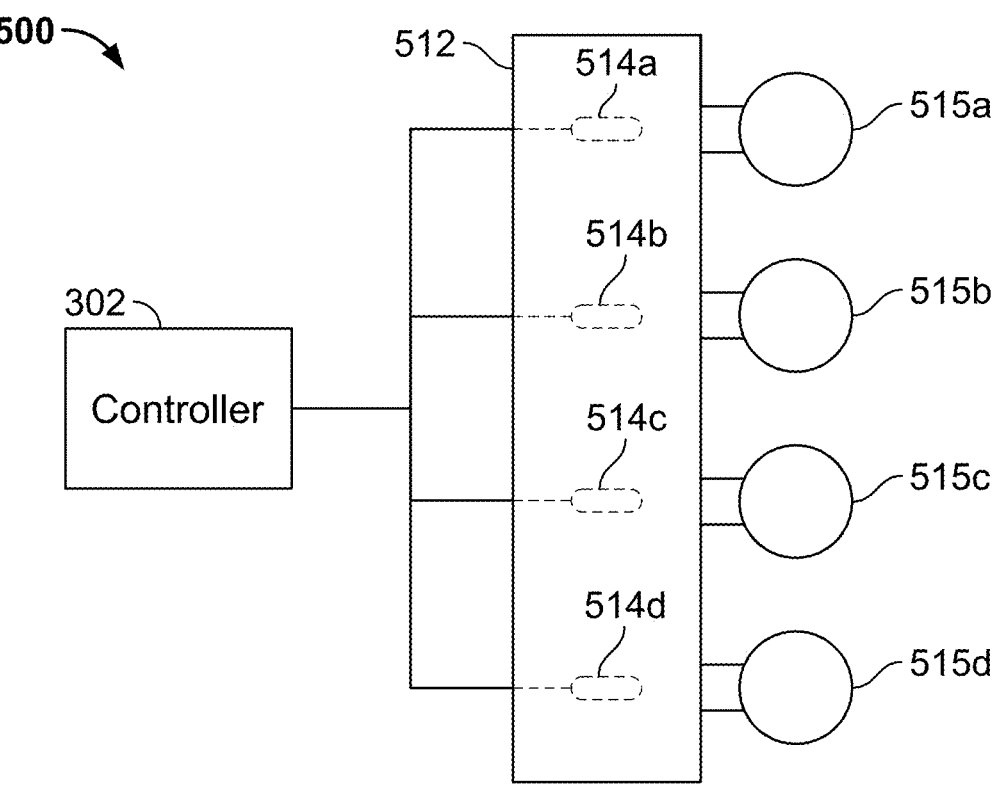
FIG. 5A is a top-down view of a cluster airlift bioreactor in accordance with some embodiments.
Figure 5B:
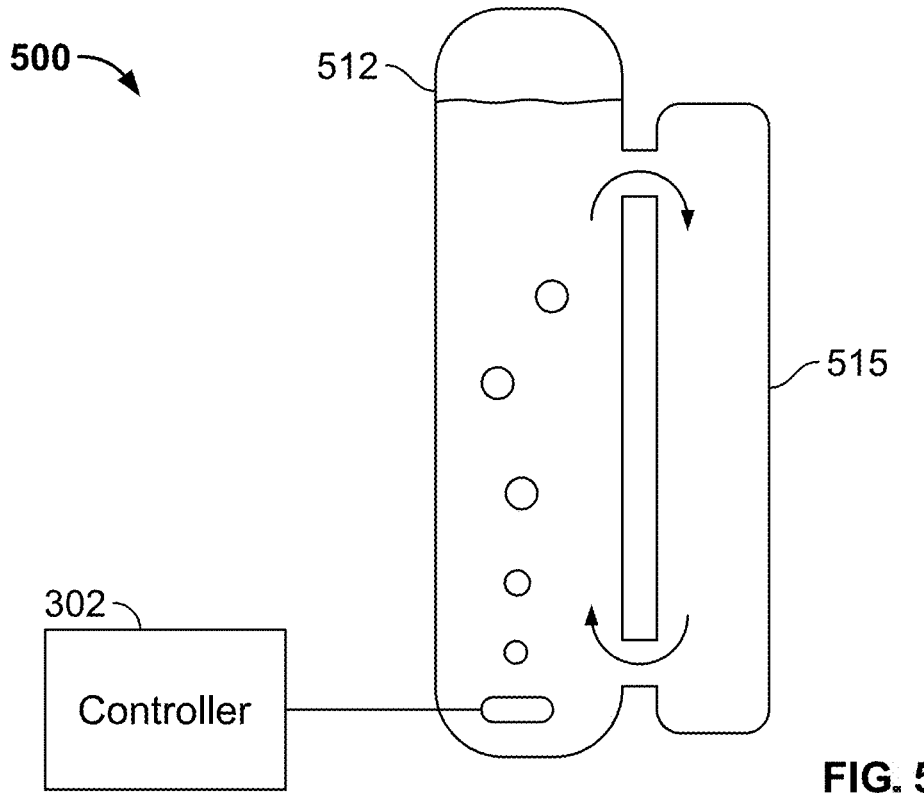
FIG. 5B is a side view of a cluster airlift bioreactor in accordance with some embodiments.

FIG. 5A is a top-down view of a cluster airlift bioreactor in accordance with some embodiments. FIG. 5B is a side view of a cluster airlift bioreactor in accordance with some embodiments. In the example shown, controller 302 is coupled to the vessel 512 of the cluster airlift bioreactor 500 via spargers 514a, 514b, 514c, 514d. In some embodiments, controller 302 is configured to individually increase or decrease a sparging rate associated with one of the spargers 514a, 514b, 414c, 414d. In some embodiments, controller 502 is configured to jointly increase or decrease a sparging rate associated with the spargers 514a, 514b, 514c, 514d inside vessel 512 (e.g., sparging region). Each of the spargers 514a, 514b, 514c, 514d is associated with a corresponding external airlift tube 515a, 515b, 515c, 515d. In some embodiments, the external airlift tubes 515a, 515b, 515c, 515d correspond to a downcomer portion (e.g., return region 515) of corresponding vertical circulation loops. In some embodiments, the external airlift tubes 515a, 515b, 515c, 515d correspond to a riser portion of corresponding vertical circulation loops. Mounting the airlift tubes 515a, 515b, 515c, 515d external to the vessel 512 enables the cluster airlift bioreactor to be easily cleaned. Although cluster airlift bioreactor 500 is depicted as having four airlift tubes, cluster airlift bioreactor 500 may include n airlift tubes.

Figure 6A:
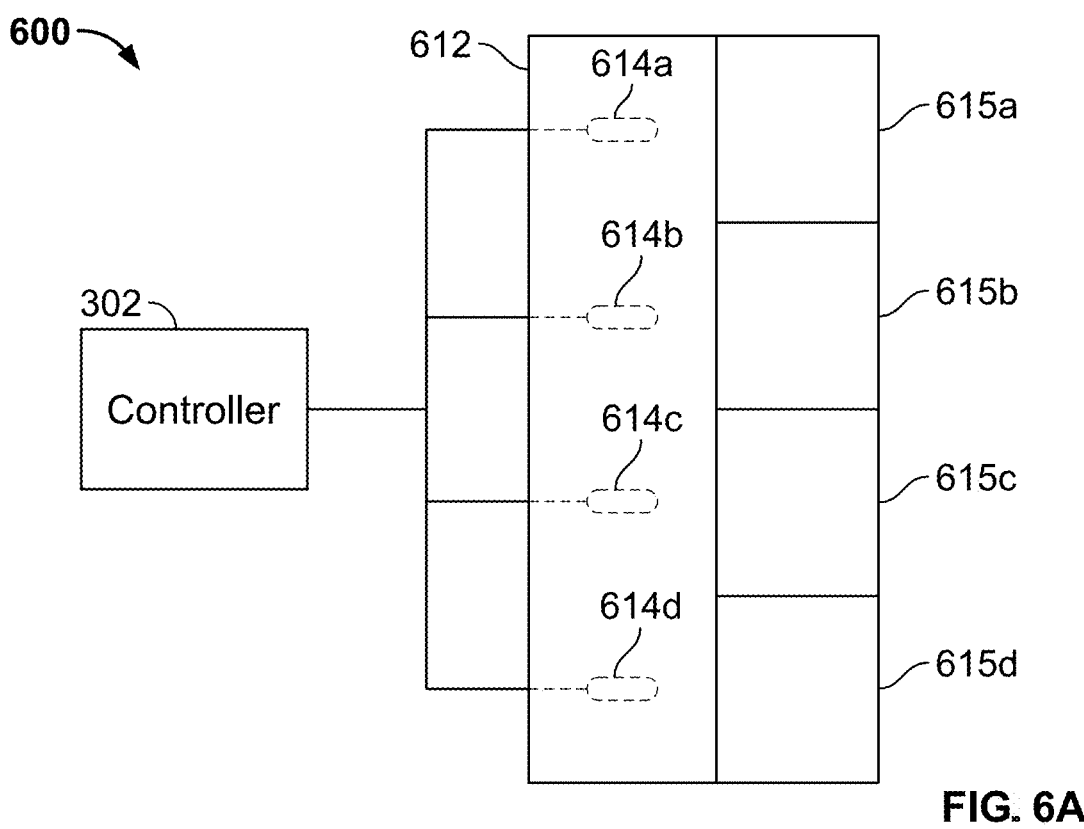
FIG. 6A is a top-down view of a cluster airlift bioreactor in accordance with some embodiments.
Figure 6B:
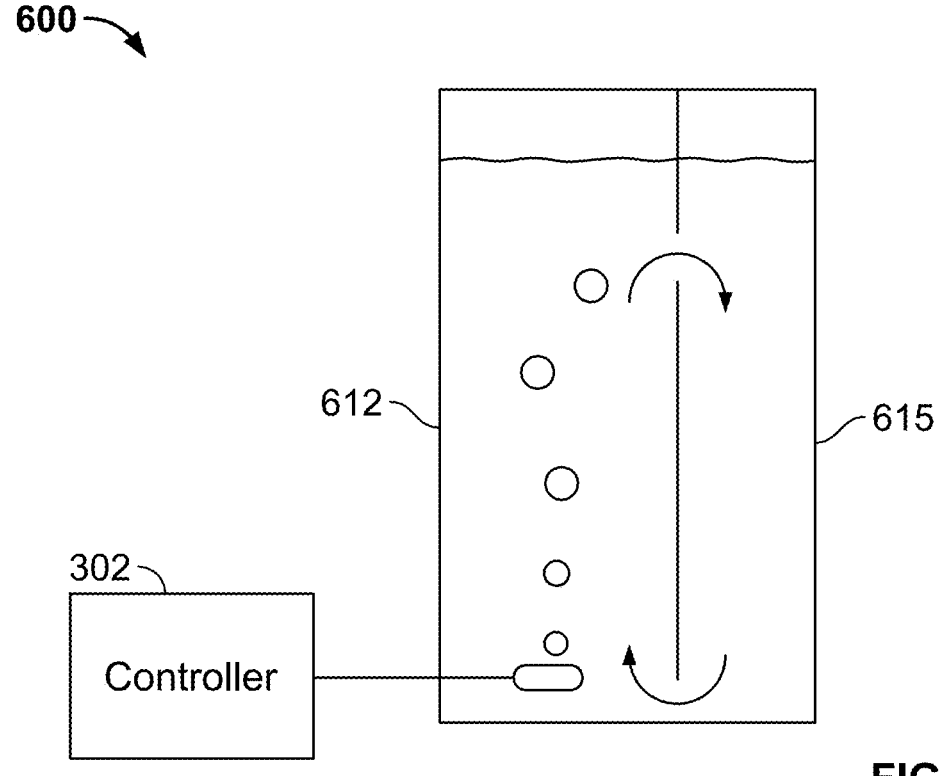
FIG. 6B is a side view of a cluster airlift bioreactor in accordance with some embodiments.

FIG. 6A is a top-down view of a cluster airlift bioreactor in accordance with some embodiments. FIG. 6B is a side view of a cluster airlift bioreactor in accordance with some embodiments. The rectangular-shaped bioreactor offers maximum cell culture volume under given footprint and height constraints. In the example shown, controller 302 is coupled to the vessel 612 of the cluster airlift bioreactor 600 via spargers 614a, 614b, 614c, 614d. In some embodiments, controller 302 is configured to individually increase or decrease a sparging rate associated with one of the spargers 614a, 614b, 614c, 614d. In some embodiments, controller 602 is configured to jointly increase or decrease a sparging rate associated with the spargers 614a, 614b, 614c, 614d. Each of the spargers 614a, 614b, 614c, 614d is associated with a corresponding external airlift tube 615a, 615b, 615c, 615d. In some embodiments, the external airlift tubes 615a, 615b, 615c, 615d correspond to a downcomer portion of corresponding vertical circulation loops. In some embodiments, the external airlift tubes 615a, 615b, 615c, 615d correspond to a riser portion of corresponding vertical circulation loops. Although cluster airlift bioreactor 600 is depicted as having four airlift tubes, cluster airlift bioreactor 600 may include n airlift tubes. Cluster airlift bioreactor 600 is similar to cluster airlift bioreactor 500 except that the external airlift tubes 615a, 615b, 615c, 615d are rectangular in shape instead of being cylindrical in shape.

Figure 7A:
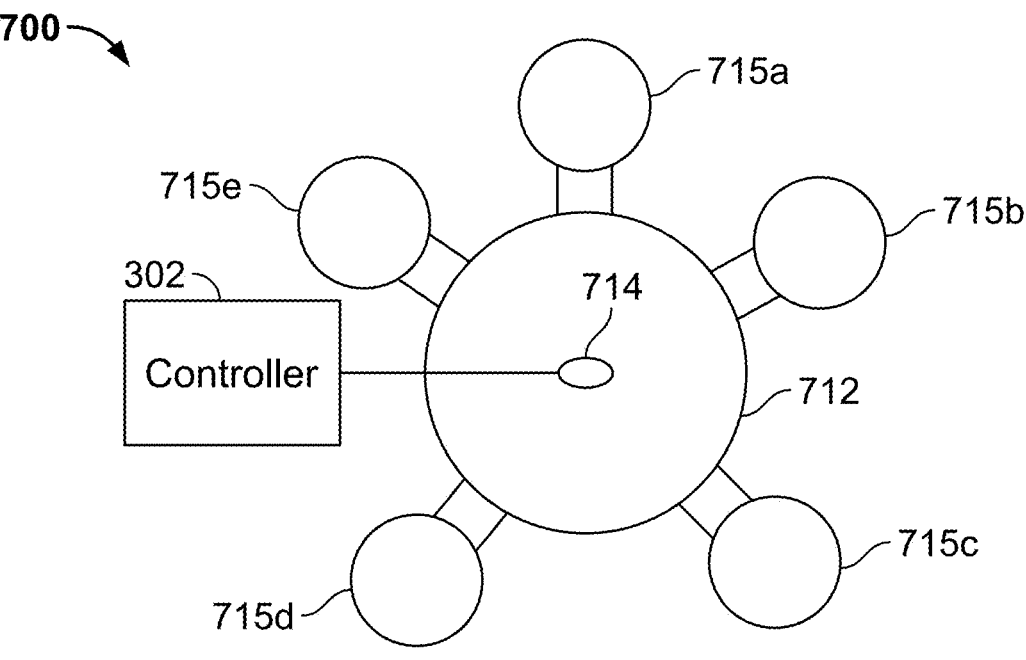
FIG. 7A is a top-down view of a cluster airlift bioreactor in accordance with some embodiments.
Figure 7B:
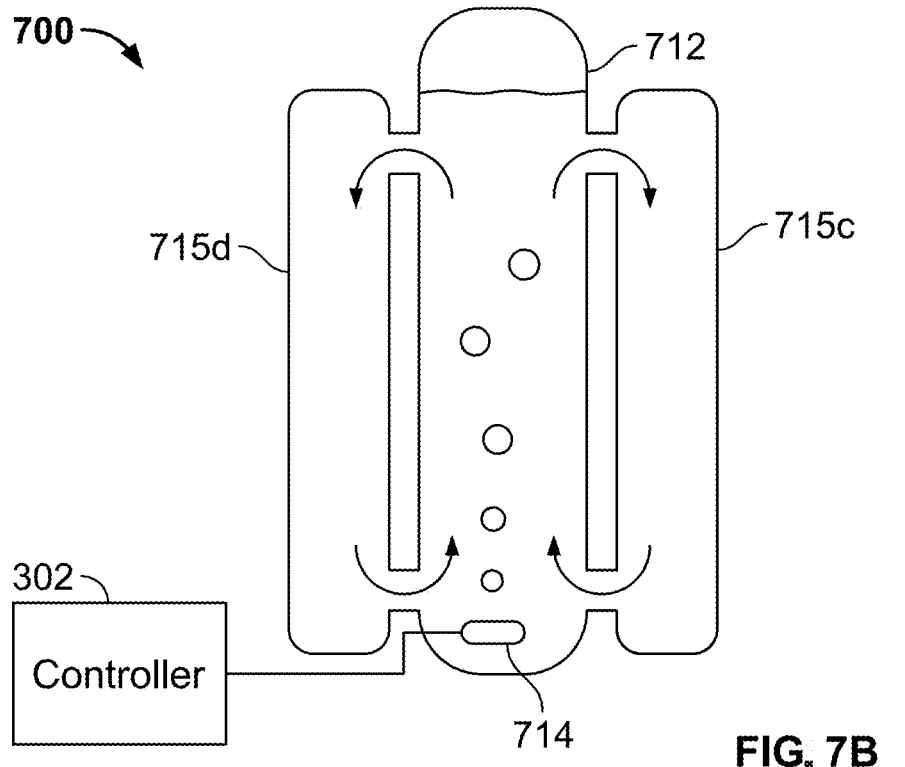
FIG. 7B is a side view of a cluster airlift bioreactor in accordance with some embodiments.

FIG. 7A is a top-down view of a cluster airlift bioreactor in accordance with some embodiments. FIG. 7B is a side view of a cluster airlift bioreactor in accordance with some embodiments. Some of the external loops could be closed off at the beginning of a batch and opened one-by-one during the batch. This design supports fed-batch cell culture without large changes in fill level. In the example shown, controller 302 is coupled to the vessel 712 of the cluster airlift bioreactor 700 via sparger 714. Controller 302 is configured to increase or decrease a sparging rate associated with sparger 714. Spargers 714 is associated with a plurality of external airlift tubes 715a, 715b, 715c, 715d, 715e. In some embodiments, the external airlift tubes 715a, 715b, 715c, 715d, 715e correspond to a downcomer portion of corresponding vertical circulation loops. In some embodiments, the external airlift tubes 715a, 715b, 715c, 715d, 715e correspond to a riser portion of corresponding vertical circulation loops.

Figure 8:
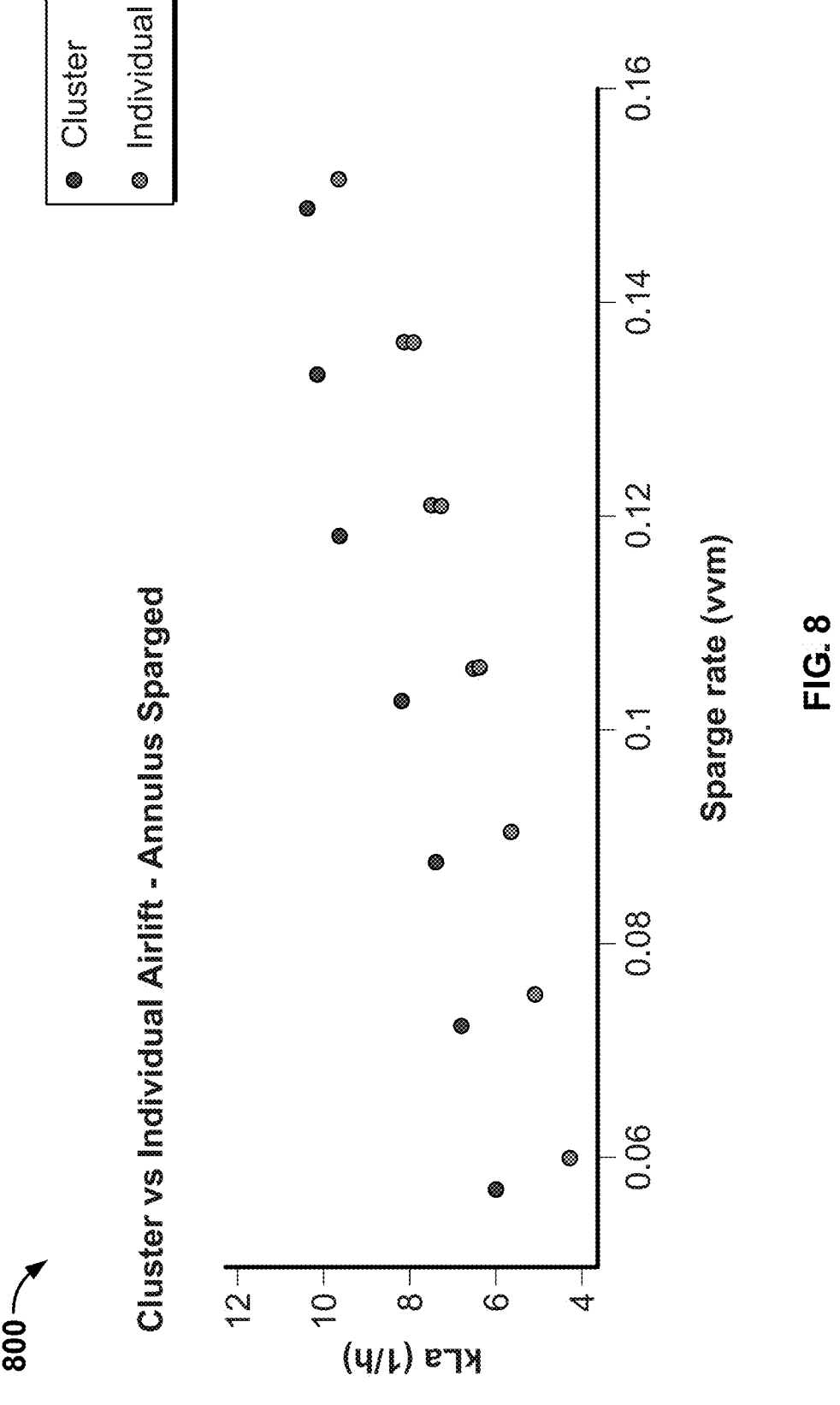
FIG. 8 is a chart comparing a mass transfer coefficient associated with an individual airlift bioreactor and a cluster airlift bioreactor in accordance with some embodiments.

FIG. 8 is a chart comparing a mass transfer coefficient associated with an individual airlift bioreactor and a cluster airlift bioreactor in accordance with some embodiments. In the example shown, chart 800 compares the performance of an individual airlift bioreactor that includes a single airlift tube having a particular height-to-diameter ratio of the tube and cross-sectional area ratio between the tube and annulus to the performance of a cluster airlift bioreactor having four airlift tubes having particular height-to-diameter ratio of the tube and a ratio of the cross-sectional area of the sum of all tubes over the cross-section area of the annulus region that matches the cross-sectional area ratio between the tube and annulus of the individual airlift bioreactor. Chart 800 illustrates that as the sparge rate of the airlift bioreactors increase, the mass transfer coefficient of the individual airlift bioreactor and the cluster airlift bioreactor both increase and are within a threshold of each other. A performance of the cluster airlift bioreactor is slightly better than the performance of the individual airlift bioreactor when both airlift bioreactors are annulus sparged.

Figure 9:
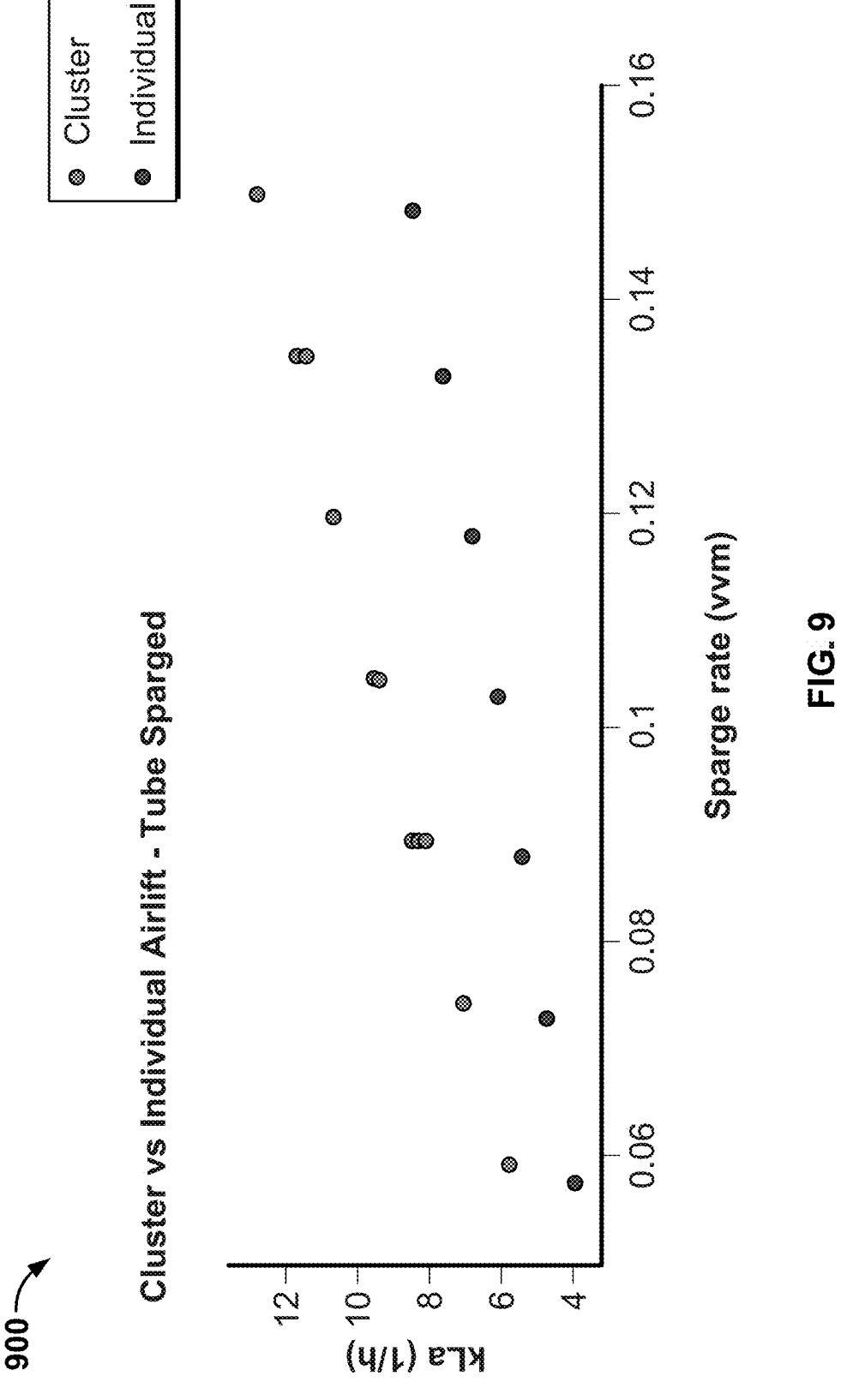
FIG. 9 is a chart comparing a mass transfer coefficient associated with an individual airlift bioreactor and a cluster airlift bioreactor in accordance with some embodiments.

FIG. 9 is a chart comparing a mass transfer coefficient associated with an individual airlift bioreactor and a cluster airlift bioreactor in accordance with some embodiments. In the example shown, chart 900 compares the performance of an individual airlift bioreactor that includes a single airlift tube having a particular height-to-diameter ratio of the tube and cross-sectional area ratio between the tube and annulus to the performance of a cluster airlift bioreactor having four airlift tubes having particular height-to-diameter ratio of the tube and a ratio of the cross-sectional area of the sum of all tubes over the cross-section area of the annulus region that matches the cross-sectional area ratio between the tube and annulus of the individual airlift bioreactor. Chart 900 illustrates that as the sparge rate of the airlift bioreactors increase, the mass transfer coefficient of the individual airlift bioreactor and the cumulative mass transfer coefficient of the cluster airlift bioreactor both increase and are within a threshold of each other. However, in contrast to chart 800, a performance of the individual airlift bioreactor is slightly better than the performance of the cluster airlift bioreactor when both airlift bioreactors are tube sparged.

The difference in performance depicted in FIGS. 8 and 9 can be explained by different drilled hole sizes used for the spargers. This difference results in different bubble sizes which impact the mass transfer coefficient. In annulus sparged mode, the cluster airlift bioreactor improved mass transfer across a range of sparge rates. In tube-sparged mode, the single airlift bioreactor performed better than the cluster airlift bioreactor. Table 1 lists the characteristics associated with the single airlift bioreactor and the cluster airlift bioreactor that generated the results of charts 800, 900.

TABLE 1

|  | Individual | Cluster |
| --- | --- | --- |
| Volume (L) | 16 | 67 |
| Annulus Radius (inch) | 2.5 | 5 |
| Number of tubes | 1 | 4 |
| Liquid height (inch) | 52 | 52 |

FIG. 10A depicts a top-down view of a cluster airlift bioreactor in accordance with some embodiments. FIG. 10B depicts a side view of a cluster airlift bioreactor in accordance with some embodiments. In the example shown, cluster airlift bioreactor 1000 includes a corresponding tube sparger located in the center of each of the tubes. Gas is supplied to each of the tube spargers 1003a, 1003b, 1003c, 1003d from one or more gas supply lines 1013a, 1013b.

FIG. 10C depicts a top-down view of a cluster airlift bioreactor in accordance with some embodiments. FIG. 10D depicts a side view of a cluster airlift bioreactor in accordance with some embodiments. In the example shown, cluster airlift bioreactor 1050 includes a corresponding ring sparger that surrounds a tube. Gas is supplied to each of the ring spargers 1054a, 1054b, 1054c, 1054d from one or more gas supply lines 1063a, 1063b.

In some embodiments, the tubes of a cluster airlift bioreactor are both tube sparged and annular sparged using a dual sparger airlift bioreactor.

Since the airlift bioreactors disclosed herein do not have an agitator, they also significantly reduce the cost and contamination risk associated with the agitator, making it an attractive alternative to stirred tank bioreactors.

Figure 11A:
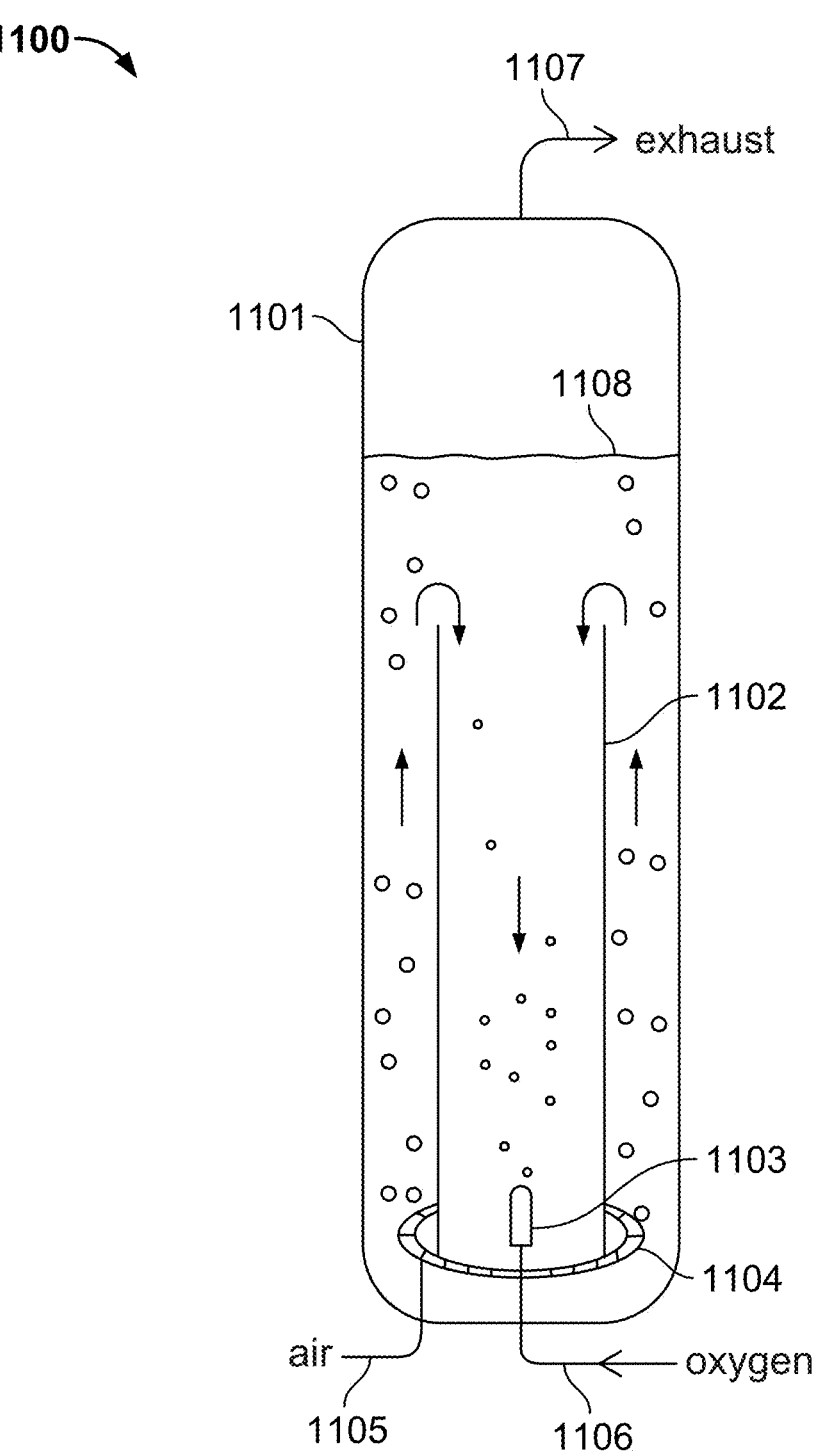
FIG. 11A is a diagram illustrating a dual sparger airlift bioreactor in accordance with some embodiments.

FIG. 11A is a diagram illustrating a dual sparger airlift bioreactor in accordance with some embodiments. The dual sparger airlift bioreactor 1100 includes vessel 1101 having a particular shape and an inner tube 1102. Vessel 1101 may have a cylindrical shape, a rectangular shape, a triangular shape, a square shape, a pentagon shape, a hexagon shape, a heptagon shape, an octagon shape, a nonagon shape, a decagon shape, or any other shape. A first gas, such as oxygen, may be introduced into the dual sparger airlift bioreactor 1100 by a first manifold 1106 and sparged inside the inner tube 1102 via sparger 1103. Sparger 1103 supplies oxygen that cells need to stay alive and grow. A second gas, such as air, may be introduced into the dual sparger airlift bioreactor 1100 by a second manifold 1105 and sparged in the annulus space via sparger 1104. The air is used primarily to sweep $dCO_2$ from the culture; it also supplements some oxygen to the cells. The dual sparger airlift bioreactor 1100 maximizes oxygen transfer efficiency without net increasing sparging rate and enables high-density cell culture under gentle conditions for better cell health. The dual sparger airlift bioreactor 1100 may be used to cultivate meat production of mammalian, avian, fish, reptile, crustacean, mollusca cell mass for human or animal consumption. The dual sparger airlift bioreactor 1100 may be used for cellular agriculture of plant cells to replace conventional production. The dual sparger airlift bioreactor 1100 may be used for biopharmaceutical culture of rodent, primate, and insect cells for production of cell therapy, gene therapy, antibody, nanobody, enzyme, fusion protein, and vaccine. The dual sparger airlift bioreactor 1100 leverages the sparging gas efficiently and strikes a good balance between the two competing objectives, i.e., low stress to cells versus good mass transfer/mixing. The dual sparger airlift bioreactor 1100 also reduces energy consumption and gas cost.

To have good liquid circulation and mixing time, the airlift tube 1102 diameter should be between 0.5~0.85 of the inner diameter for the airlifting section of the dual sparger airlift bioreactor 1100. In other words, the airlift tube cross-sectional area should be between 25%~72% of that the bioreactor cross-sectional area if the airlift bioreactor is not perfectly cylindrical. Note that this range does not apply to the wider bubble separator section of a bioreactor if it has one. The height of airlift tube 1102 may be between 2-40 feet to take advantage of the benefit described herein. The lower end 2~20 ft is ideal for a bioreactor with sintered or small drilled-hole in the downcomer; while the higher end 10~40 ft is ideal for a bioreactor with a drilled-hole or open pipe sparger in the downcomer.

In any bioreactor, cells need nutrients from cell culture media. In some embodiments, the cells are mammalian, avian, fish, reptile, crustacean, or mollusca cells. In some embodiments, the cells are plant cells. In some embodiments, the cells are rodent, primate, or insect cells. In addition, cells also consume oxygen and produce carbon dioxide. As a metabolic waste, the excessive accumulation of carbon dioxide will harm cell health and acidify the media. Note that a moderate level of dissolved carbon dioxide is acceptable and even beneficiary to maintain pH of cell culture media. Carbon dioxide may be removed from the dual sparger airlift bioreactor 1100 via exhaust 1107.

In an airlift bioreactor, sparging gases have three main jobs: 1) provide a good mixing; 2) provide oxygen for cells to consume; 3) sweep away carbon dioxide waste that cells produce. The sparging gases drive a liquid circulation loop between the riser, the downcomer, and the two sections above and below the airlift tube. Fast liquid circulation results in good mixing and minimizes uneven distribution of nutrients, oxygen, carbon dioxide, metabolic waste, titrant, and temperature. Oxygen and carbon dioxide have very different solubility and Henry's coefficient. As a result, their mass transfer behaviors in cell culture are distinctly different.

For the dual sparger airlift bioreactor 1100 to work effectively, the two spargers play different roles. One sparger delivers a significantly higher sparging gas flow rate than the other. It drives the liquid recirculation and mixing. The liquid rises in the area above this sparger, so this area is called the riser. In the riser, sparging gas could be a different mix at a different stage of cell culture: nitrogen/air/co2 mix at the lower stage, air at the high-density stage, or air/oxygen mix for ultra-high density stage. The other sparger delivers far less sparging flow rate. It generates some lifting power but cannot compete with the sparger in the riser. The liquid sinks in this area, thus, it is called the downcomer. In the downcomer, the sparging gas may be enriched oxygen or pure oxygen. In some embodiments, sparger 1104 delivers a significantly higher sparger gas flow rate (e.g., greater than a threshold amount) than sparger 1103. In some embodiments, sparger 1103 delivers a significantly higher sparger gas flow rate than sparger 1104. The dual sparger design leverages the different hydraulic characteristics of the riser and the downcomer and matches them with the oxygen transfer and carbon dioxide sweep requirements.

In the riser, the gas bubble residence time is short due to the high compound velocity of bulk liquid rising and gas bubble rising due to buoyancy. The high flow rate and short residence time make it ideal to play the dominant role in carbon dioxide sweeping. In the downcomer, the gas bubbles rise against the bulk liquid. By carefully balancing them, the gas bubbles can have a much longer residence time, which is very helpful in boosting oxygen transfer. As a result, less sparging gas is needed to achieve the same oxygen transfer requirement. This is particularly important when trying to achieve high cell density.

Note that the sparging in the riser also contributes to oxygen transfer, and similarly the sparging in the downcomer also contributes to carbon dioxide sweep. Their contributions are not neglectable, just less dominant comparatively.

By separating the oxygen transfer and carbon dioxide sweep, the dual sparger design not only uses the gases efficiently for oxygen transfer and carbon dioxide sweep (thus, minimizes cell damage from unnecessarily high sparging flow rate), but also decouples the dissolved oxygen and dissolved carbon dioxide control loops in the bioreactor automation scheme. The decoupling of the two needs simplifies automation, gives a greater degree of freedom in cell culture process design, eliminates the dilemma of dealing with competing objectives, and lifts a major barrier that gets in the way of achieving high cell density. Control of dissolved gas concentration is predominantly influenced by mass transfer and limited by mass balance. Mass transfer is dependent on the surface area, concentration difference between the gaseous and liquid phases, and available time (bubble residence time) for mass transfer.

Mixing time and mass transfer in an airlift bioreactor are primarily influenced by the difference in gas holdup between the riser and downcomer. When there is a difference in gas holdup between the two volumes, it creates a difference in density that generates a driving force for liquid movement proportional to the difference. The liquid velocity in the riser and downcomer affect the bioreactor mixing time and bubble residence time. The bubble residence time had direct impact on mass transfer efficiency.

For typical cell culture, a bioreactor needs many times more air and/or nitrogen flow rate to sweep dCO2 than the need for oxygen. Therefore, the air-liquid mix in the annular space of dual sparger airlift bioreactor 1100 will be much lighter than the oxygen-liquid mix in the inner tube 1102. The recirculating flow depicted in FIG. 11A flows in a reversed direction when compared with the recirculating flow depicted in FIG. 1. The liquid (e.g., cell culture media) comes down in the inner tube 1102 and opposes the rising oxygen bubble. The oxygen bubbles will be slowed down or trapped in the inner tube 1102. The increased residence time of oxygen bubbles in the inner tube will greatly enhance mass transfer. Smaller oxygen bubbles will quickly shrink in size or even completely dissolve in liquid. As a result, oxygen utilization could be greatly improved, even approaching the theoretical limit (i.e., all inputted oxygen is consumed by the cells). The high oxygen transfer efficiency reduces oxygen demand and minimizes the cell damage from oxygen bubbles bursting when they reach the liquid surface 1108. The dual sparger airlift bioreactor design enables high-density cell culture while maintaining a gentle condition for cells, solving a big challenge facing the scale-up of conventional stirred tanks and airlift bioreactors. The optimal aspect ratio of the airlift tube height to its inner diameter is between 5-10. The liquid height 1108 from the bottom of the airlift tube to the bottom of the bioreactor should be anywhere between 0.25~1.0 of the airlift tube's inner diameter. The lower end 0.25~0.5 is ideal for cell culture in the form of aggregates and microcarriers; while the higher end 0.35~1.0 is ideal for the suspension cell culture.

Using a counterflow to slow down or trap oxygen bubbles, dual-sparged airlift bioreactor 1100 and its variations boost oxygen mass transfer and minimize the sparging demand, creating a healthy environment for cells to grow and proliferate. These airlift bioreactors overcome one of the major obstacles that prevent high cell density in large bioreactors.

Figure 11B:
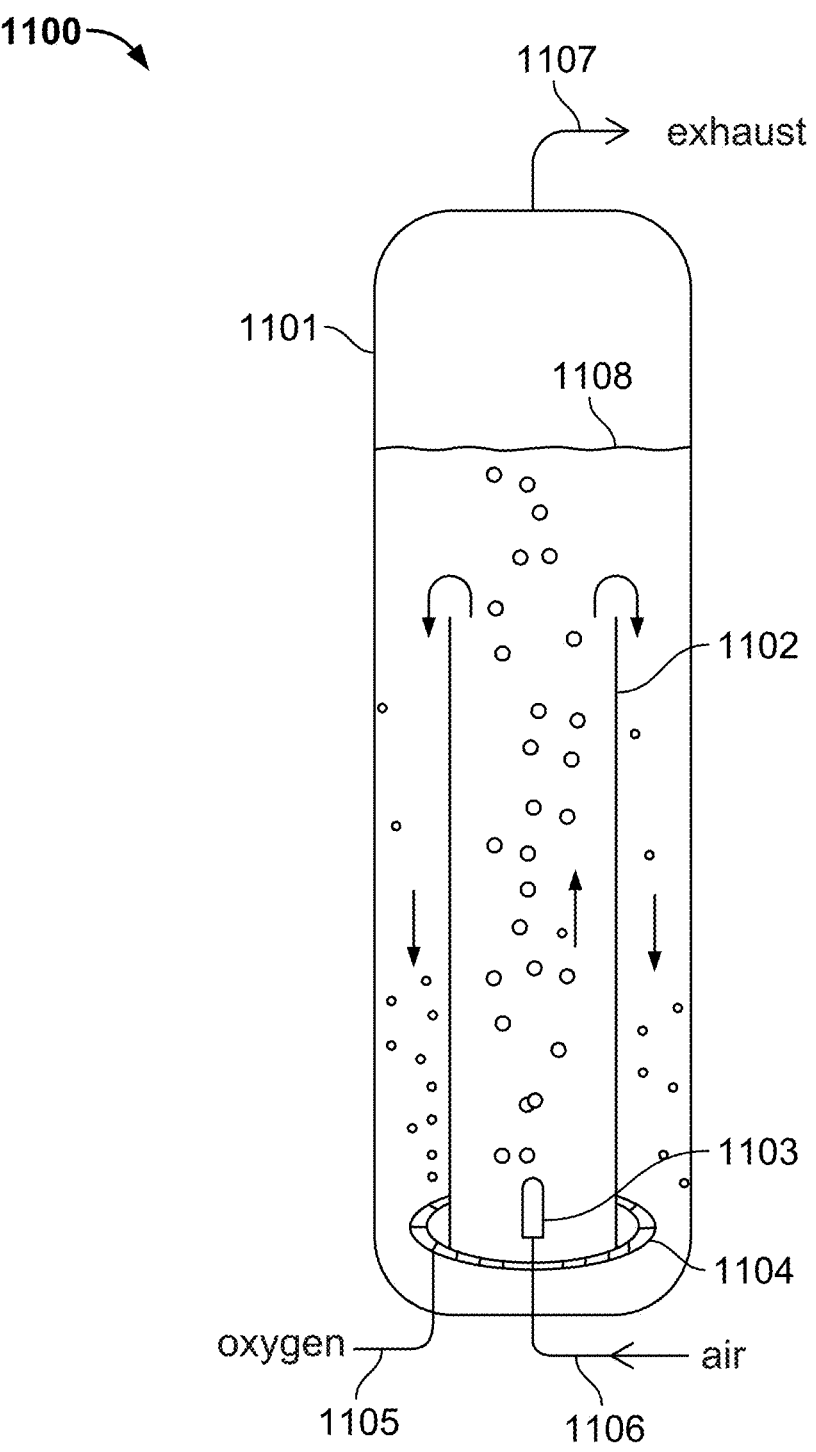
FIG. 11B is a diagram illustrating a dual sparger airlift bioreactor in accordance with some embodiments.

The riser and downcomer designation are decided by the operation condition, not the hardware. One can flip the roles by adjusting the sparging flow rate. For example, FIG. 11B illustrates the dual sparger airlift bioreactor 1100 where the rise and downcomer roles have been flipped when compared with the dual sparge airlift bioreactor of FIG. 11A. A first gas, such as air, is introduced into the dual sparger airlift bioreactor 1100 by a first manifold 1106 and sparged inside the inner tube 1102 via sparger 1103. The air is used primarily to sweep $dCO_2$ from the culture; it also supplements some oxygen to the cells. A second gas, such as oxygen, is introduced into the dual sparger airlift bioreactor 1100 by a second manifold 1105 and sparged in the annulus space via sparger 1104. Sparger 1104 supplies oxygen that cells need to stay alive and grow. The riser is located in the inner tube 1102 and the downcomer is located in the annulus space of dual sparger airlift bioreactor 1100.

To leverage the full advantage of the dual sparger design, closely competing sparging between the two spargers shall be avoided. Under those conditions, the liquid circulation is weakened and bioreactor mixing behavior will deteriorate, and mass transfer efficiency will also suffer. Another extreme to avoid is the liquid velocity in the downcomer is so high, it drives the gas bubbles in the downcomer downward and forces them to rise in the riser, thus reducing the oxygen transfer efficiency. This phenomenon is more likely to happen in an airlift bioreactor with a very tall airlift tube.

Figure 12C:
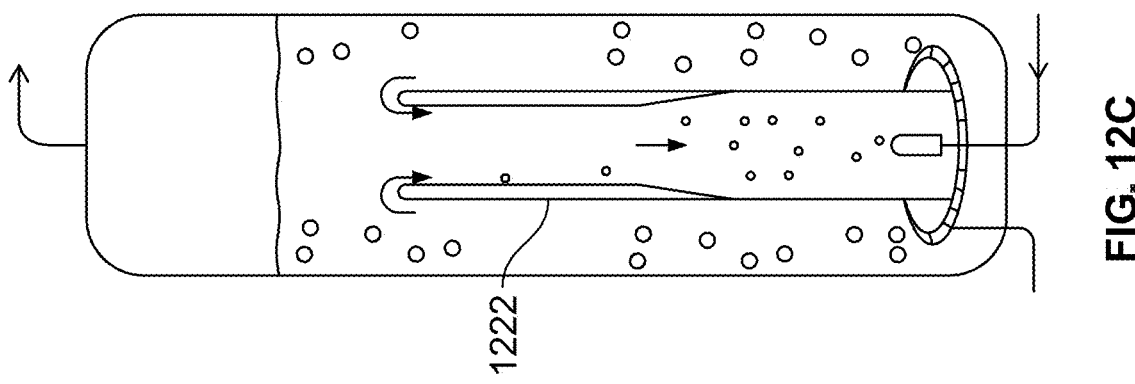
FIG. 12C is a diagram illustrating a dual sparger airlift bioreactor in accordance with some embodiments.
Figure 12B:
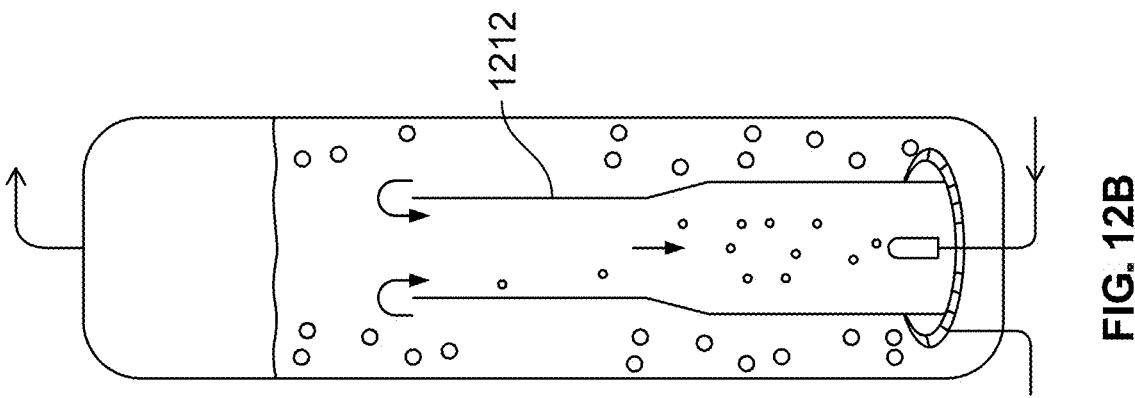
FIG. 12B is a diagram illustrating a dual sparger airlift bioreactor in accordance with some embodiments.
Figure 12A:
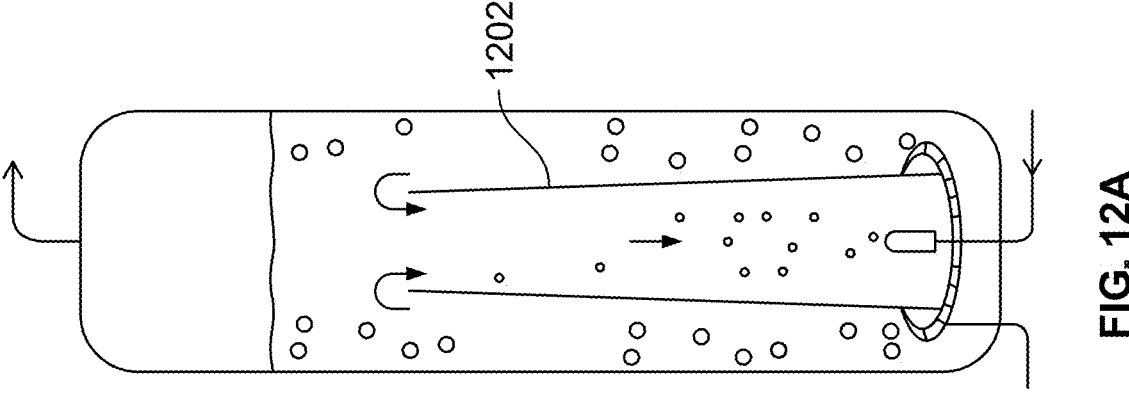
FIG. 12A is a diagram illustrating a dual sparger airlift bioreactor in accordance with some embodiments.

The bioreactor sparger often produces bubbles with a range of sizes. Different size bubbles rise at different velocities, making it less obvious to fine-tune the control. By altering the cross section of center tube 1102 to become the center tube 1202 of FIG. 12A, the center tube 1212 of FIG. 12B, or the center tube 1222 of FIG. 12C, a wider range of oxygen bubbles could be slowed down or trapped. Note that the annular and center space cross-section, as seen in FIG. 12C, can be independently adjusted, e.g., the annular space remains constant while the center chamber has a gradual step change. The same varying cross-sectional area concept can apply to center-sparging dominated scenarios and to external circulating airlifting bioreactor scenarios.

Figure 13B:
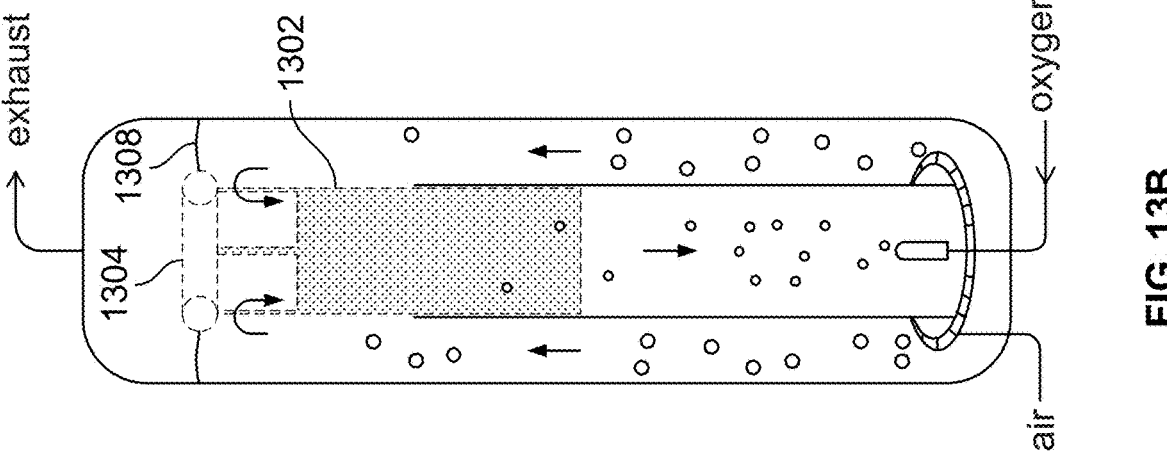
FIG. 13B is a diagram illustrating a dual sparger airlift bioreactor in accordance with some embodiments.
Figure 13A:
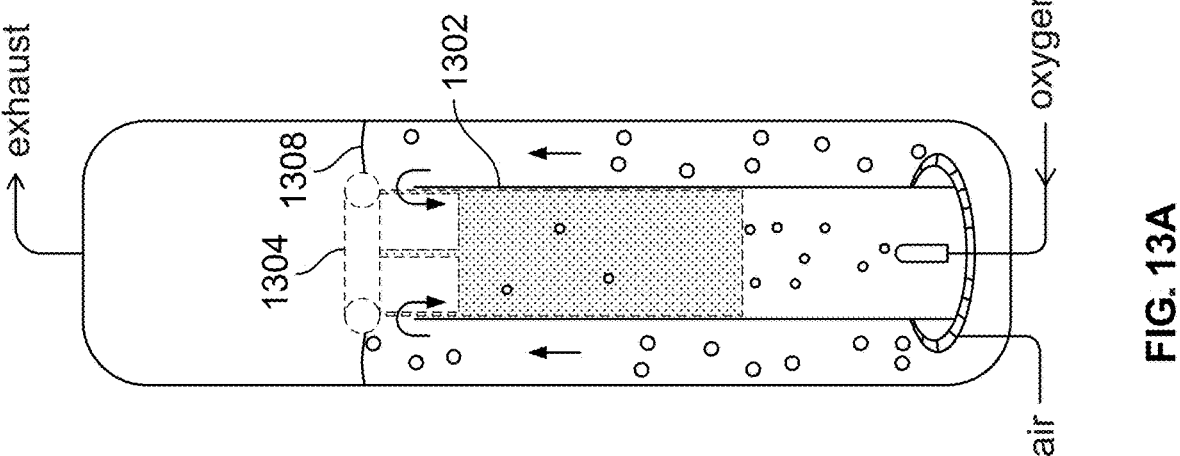
FIG. 13A is a diagram illustrating a dual sparger airlift bioreactor in accordance with some embodiments.

In some embodiments, one or more additional feeds are added to the dual sparger airlift bioreactor 1100. A floating center-tube extender 1302 may be added to the dual sparger airlift bioreactor 1100 to automatically adapt to increasing liquid levels in the dual sparger airlift bioreactor 1100. This design well suits bed-bath cell culture where the bioreactor working volume changes over the course of a batch. As seen in FIGS. 13A and 13B, the floating center-tube extender 1302 rises as a level of a liquid 1308 rises. No mechanically actuated mechanism is needed. The floating device 1304 may be a hollow ring or other shapes or forms that provide a center-balanced buoyance force.

Figure 14A:
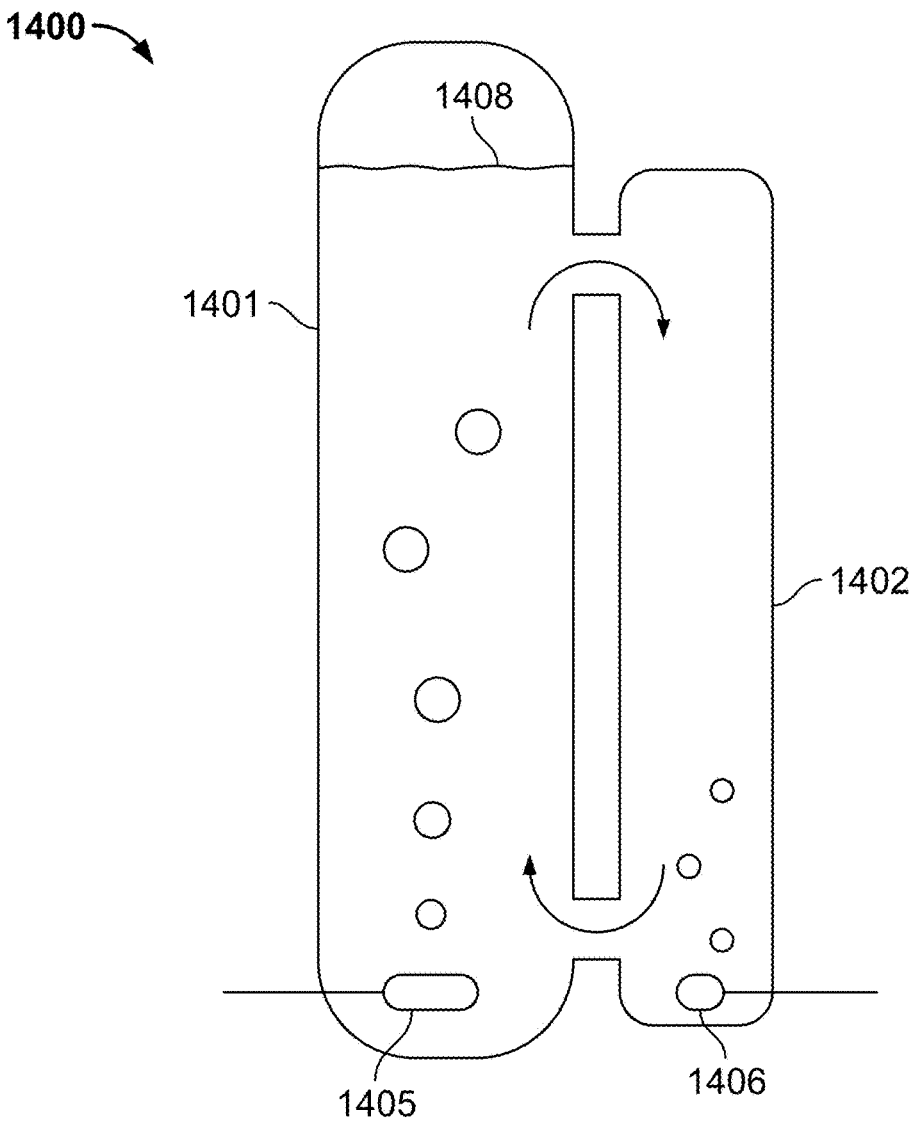
FIG. 14A illustrates a side view of a dual sparger airlift bioreactor in accordance with some embodiments.
Figure 14B:
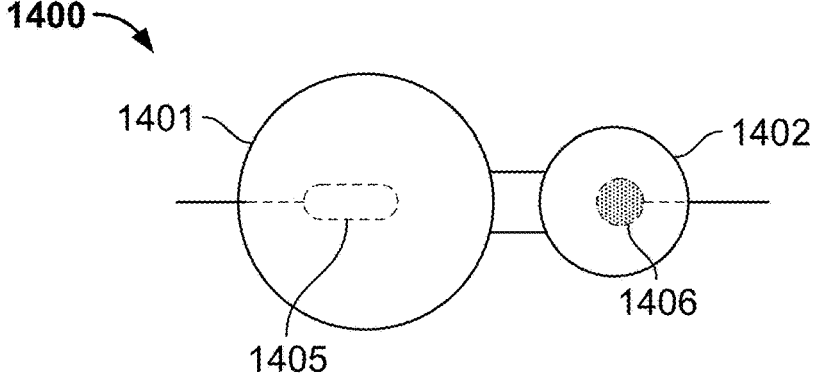
FIG. 14B illustrates a top-down view of a dual sparger airlift bioreactor in accordance with some embodiments.

The dual sparger airlifting design also applies to external loop airlift bioreactors where the riser and downcomer are two separate volumes that connect in top and bottom. FIG. 14A illustrates a side view of a dual sparger airlift bioreactor in accordance with some embodiments. FIG. 14B illustrates a top-down view of a dual sparger airlift bioreactor in accordance with some embodiments. In the example shown, the dual sparger airlift bioreactor 1400 includes a vessel 1401 that includes a liquid 1408. The vessel is coupled to airlift tube 1402, which is external to vessel 1401. Vessel 1401 includes a first sparger 1405 and an airlift tube 1402 that includes a second sparger 1406. The first sparger 1405 and the second sparger 1406 are coupled to a controller (not shown). The controller is configured to control a corresponding sparging rate associated with the first sparger 1405 and the second sparger 1406. In some embodiments, the sparging rate associated with the first sparger 1405 is significantly higher (e.g., more than a threshold amount) than the second sparger 1406 such that the vessel 1401 is the riser and the airlift tube 1402 is the downcomer. In some embodiments, the sparging rate associated with the second sparger 1406 is significantly higher (e.g., more than a threshold amount) than the first sparger 1405 such that the vessel 1401 is the downcomer and the airlift tube 1402 is the riser.

Figure 15:
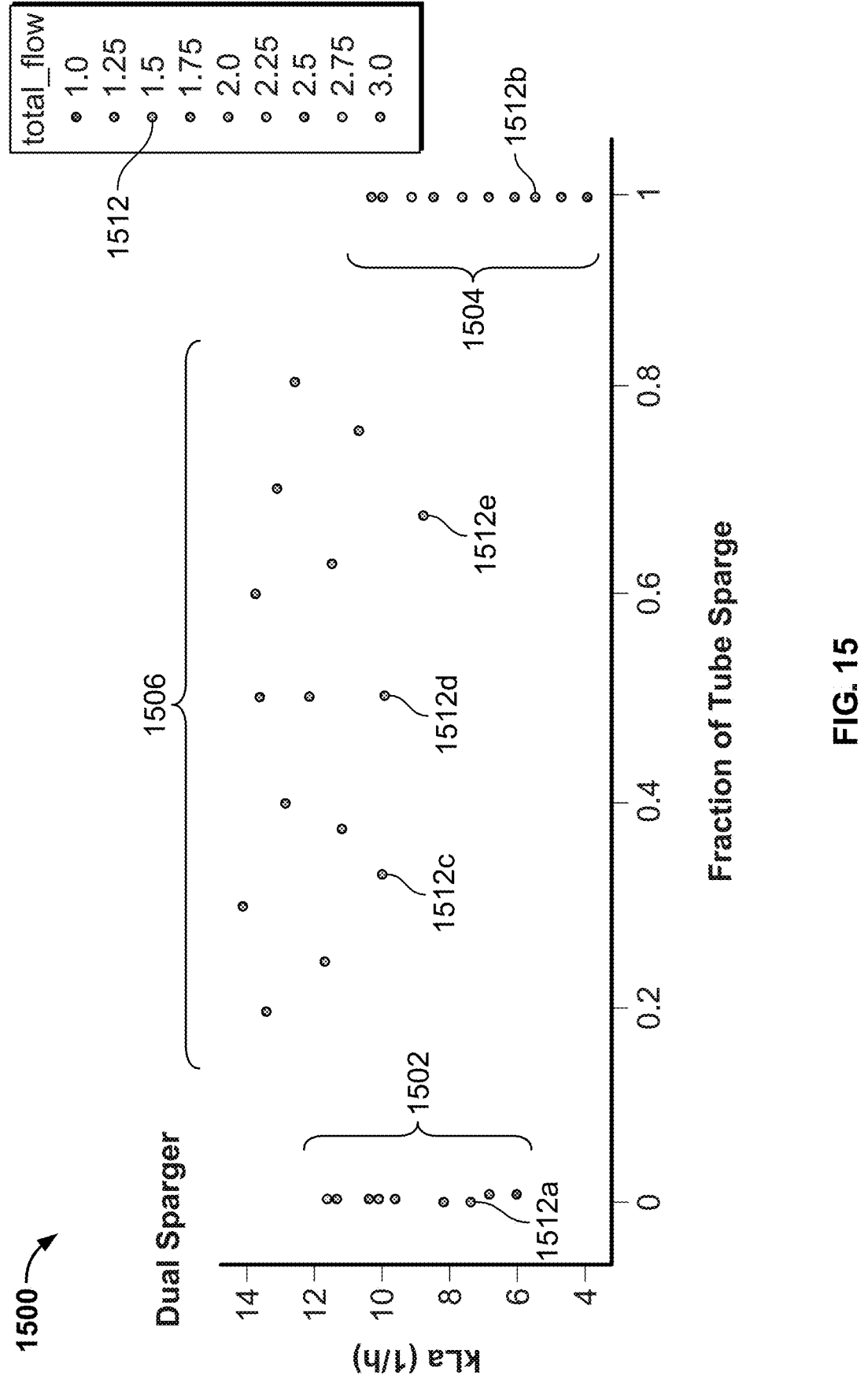
FIG. 15 is a chart comparing an annular sparged airlift bioreactor, a tube sparged airlift bioreactor, and a dual-sparged airlift bioreactor.

FIG. 15 is a chart comparing an annular sparged airlift bioreactor, a tube sparged airlift bioreactor, and a dual-sparged airlift bioreactor. In the example shown, chart 1500 includes a first group of points 1502, a second group of points 1504, and a third group of points 1506. The first group of points 1502 corresponds to an annular sparged airlift bioreactor, the second group of points 1504 corresponds to a tube sparged airlift bioreactor, and the third group of points 1506 corresponds to a dual-sparged airlift bioreactor. Chart 1500 compares a mass transfer coefficient (kLa) to a fraction of an airlift bioreactor that is tube sparged.

A plurality of points included in the first group 1502 are associated with a corresponding gas flow rate. Chart 1500 indicates the corresponding mass transfer coefficients for the gas flow rates included in the first group 1502. The plurality of points included in the first group 1502 may be associated with the dual sparger airlift being completely annulus sparged (e.g., no tube sparging) or an airlift bioreactor that is annulus sparged (e.g., airlift bioreactor 1050).

A plurality of points included in a second group 1504 are associated with a corresponding gas flow rate. Chart 1500 indicates the corresponding mass transfer coefficients for the gas flow rates included in the second group 1504. The plurality of points included in the second group 1504 are associated with the dual sparger airlift being completely tube sparged (e.g., no annulus sparging) or an airlift bioreactor that is tube sparged (e.g., airlift bioreactor 1000).

A plurality of points included in a third group 1506 are associated with a corresponding gas flow rate. Chart 1500 indicates the corresponding mass transfer coefficients for the gas flow rates included in the third group 1506. The plurality of points included in the third group 1506 are associated with an airlift bioreactor that is both tube sparged and annulus sparged. Some of the points included in the third group of points for readability purposes.

The mass transfer coefficient associated with a gas flow rate improves when the dual sparger airlift bioreactor is tube sparged and annulus sparged. In some embodiments, the dual sparger airlift bioreactor is in an annular sparge dominating mode (e.g., 0-0.5 fraction of tube sparge). In some embodiments, the dual sparger airlift bioreactor is in a tube sparge dominating mode (e.g., 0.5-1 fraction of tube sparge). As seen in chart 1500, when the dual sparger airlift bioreactor is tube sparged and annulus sparged, the mass transfer coefficient associated with gas rate 1512 may improve from the mass transfer coefficient associated with gas flow rate 1512a (100% annulus sparged) to the mass transfer coefficient associated with gas flow rate 1512c, the mass transfer coefficient associated with gas flow rate 1512d, or the mass transfer coefficient associated with gas flow rate 1512e. When the dual sparger airlift bioreactor is tube sparged and annulus sparged, the mass transfer coefficient associated with gas rate 1512 may improve from the mass transfer coefficient associated with gas flow rate 1512b (100% tube sparged) to the mass transfer coefficient associated with gas flow rate 1512c, the mass transfer coefficient associated with gas flow rate 1512d, or the mass transfer coefficient associated with gas flow rate 1512e.

The modified airlift bioreactors described above can support the culture of suspension cells, cell aggregates, or cells on microcarriers. It can also be fitted with a cell retention device to enable perfusion of cell culture.

One additional benefit of the dual sparger design is that the spargers can be used as spray balls during the clean-in-place (CIP) step between two cell culture batches, and clean the blind spots in the riser and the downcomer wall that could not be covered by conventional spray ball in the top of the bioreactor. In some embodiments, a detergent or other cleaning solution is introduced to a bioreactor via spargers 1105 to clean the annulus space. In some embodiments, a detergent or other cleaning solution is introduced to a bioreactor via sparger 1103 to clean the inner tube space.

In some embodiments, the tube sparger can take a shape of a ball, a straight line, a curved line, a ring, or any practical shape. In some embodiments, the annulus sparger can take a shape of a ball, a straight line, a curved line, a ring, or any practical shape.

Figure 16:
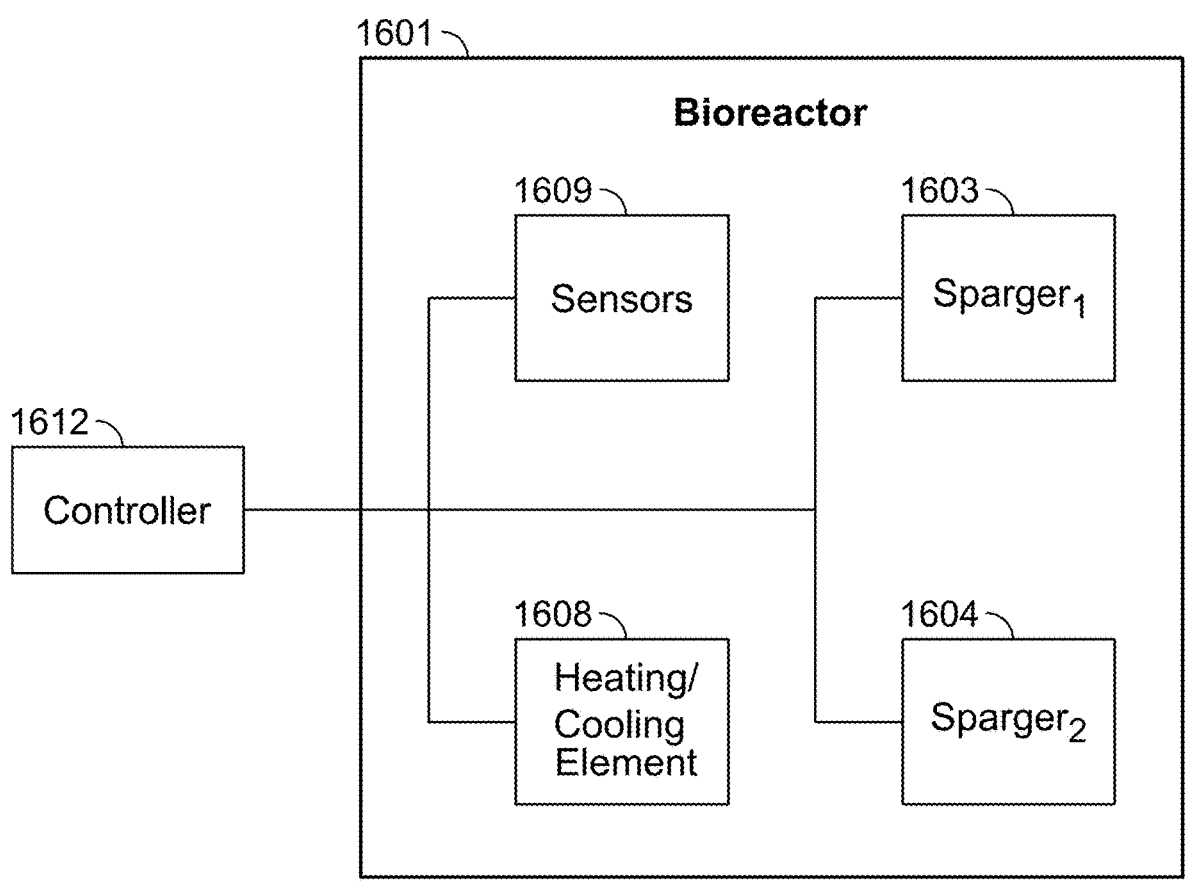
FIG. 16 is a block diagram illustrating a system for controlling a dual sparger airlift bioreactor in accordance with some embodiments.

FIG. 16 is a block diagram illustrating a system for controlling a dual sparger airlift bioreactor in accordance with some embodiments. In the example shown, the system 1600 includes a dual sparger airlift bioreactor 1601 coupled to a controller 1612. The dual sparger airlift bioreactor 1601 includes a first sparger 1603 and a second sparger 1604. A corresponding sparging rate associated with spargers 1603,

1604 is controlled by controller 1612. In some embodiments, controller 1612 controls a sparging rate associated with sparger 1603 to be higher than the sparging rate associated with sparger 1604. In some embodiments, controller 1612 controls a sparging rate associated with sparger 1604 to be higher than the sparging rate associated with sparger 1603. Controller 1612 may control a sparging rate associated with sparger 1603 to be equal to the sparging rate associated with sparger 1603, however, as discussed above, under those conditions, the liquid circulation is weakened and bioreactor mixing behavior will deteriorate, and mass transfer efficiency will also suffer. In some embodiments, controller 1612 is configured to flip the rise and downcomer roles of the annular space and inner tube spaces. In some embodiments, controller 1612 controls air/nitrogen/carbon dioxide mixing ratio and flow rate associated with sparger 1603 to target a dissolved carbon dioxide setpoint, and controls oxygen flow rate associate with sparger 1604 to target a dissolved oxygen setpoint. In some embodiments, controller 1612 controls air/nitrogen/carbon dioxide mixing ratio and flow rate associated with sparger 1604 to target a dissolved carbon dioxide setpoint, and controls oxygen flow rate associate with sparger 1603 to target a dissolved oxygen setpoint.

In some embodiments, each of the airlift tubes included in a cluster airlift bioreactor, such as cluster airlift bioreactor 150, is dual-sparged and controlled via controller 1612.

Figure 17:
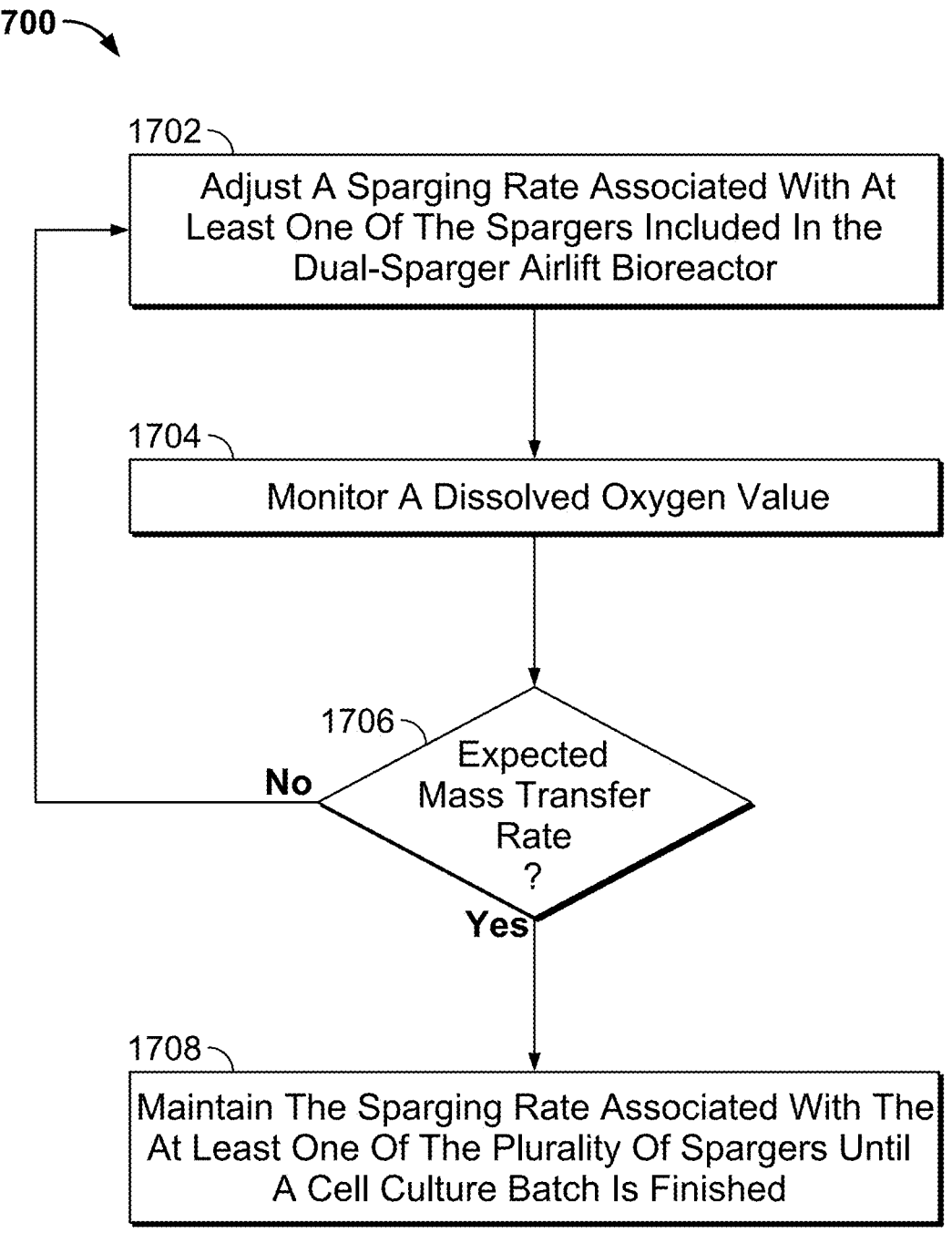
FIG. 17 is a flow diagram illustrating a process for utilizing a dual sparger airlift bioreactor in accordance with some embodiments.

FIG. 17 is a flow diagram illustrating a process for utilizing a dual sparger airlift bioreactor in accordance with some embodiments. In the example shown, process 1700 may be implemented by a controller, such as controller 1602, of an dual sparger airlift bioreactor, such as dual sparger airlift bioreactor 1100.

At 1702, a sparging rate associated with at least one of the spargers included in the dual sparger airlift bioreactor is adjusted. The dual sparger airlift bioreactor includes a tube sparger included in an inner tube and a ring-shaped sparger included in an annulus space. The sparging rate of the tube sparger and/or the ring-shaped sparger is adjusted.

At 1704, a dissolved oxygen value is monitored for a particular period of time.

At 1706, it is determined whether the mass transfer rate the expected mass transfer rate. In response to a determination that the mass transfer rate matches the expected mass transfer rate, process 1700 proceeds to 1708. In response to a determination that the mass transfer rate does not match the expected mass transfer rate, process 1700 returns to 1702.

At 1708, the sparging rate associated with the at least one of the plurality of spargers included in the dual sparger airlift bioreactor is maintained until a cell culture batch is finished.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A bioreactor, including:
   a liquid;
   one or more sensors; a plurality of spargers;
   a plurality of vertical circulation loops, wherein each of the plurality of vertical circulation loops is associated with one or more of the plurality of spargers;
   a controller coupled to the plurality of spargers and the one or more sensors, wherein the controller is configured to:

determine that a reading associated with the bioreactor is not at a setpoint;

adjust a sparging rate associated with at least one of the plurality of spargers responsive to gas sparging or a liquid additive being introduced to the bioreactor, wherein the sparging rate associated with the at least one of the plurality of spargers is adjusted from a first sparging rate to a second sparging rate; and in response to the reading associated with the bioreactor being consistent and at the setpoint, modify the sparging rate associated with the at least one of the plurality of spargers from the second sparging rate to the first sparging rate.

2. The bioreactor of claim 1, wherein a first sparger of the plurality of spargers is included in a first sparging region of a first vertical circulation loop of the plurality of vertical circulation loops.

3. The bioreactor of claim 2, wherein the first sparger is an annulus sparger.

4. The bioreactor of claim 2, wherein the first sparger is a tube sparger.

5. The bioreactor of claim 2, wherein the first sparging region is internal to the bioreactor and a first return region of the first vertical circulation loop is external to the bioreactor.

6. The bioreactor of claim 2, wherein a shape associated with the first vertical circulation loop is different than at least one or more other vertical circulation loops.

7. The bioreactor of claim 1, wherein the vertical circulation loops have a cylindrical shape, a rectangular shape, a triangular shape, a square shape, a pentagon shape, a hexagon shape, a heptagon shape, an octagon shape, a nonagon shape, and/or a decagon shape.

8. The bioreactor of claim 1, wherein the plurality of spargers include a plurality of annulus spargers and a plurality of tube spargers.

9. The bioreactor of claim 1, further comprising one or more sensors that include at least one of a pH sensor, temperature sensor, a dissolved oxygen sensor, a dissolved carbon dioxide sensor, biocapacitance sensor, a Raman sensor, and/or a near-infrared sensor.

10. The bioreactor of claim 9, wherein the controller is coupled to the one or more sensors and configured to control the plurality of spargers based on an output of the one or more sensors.

11. The bioreactor of claim 1, wherein a first vertical circulation loop of the plurality of vertical circulation loops is in liquid communication with one or more other loops of the plurality of vertical circulation loops.

12. The bioreactor of claim 11, wherein the liquid is cell culture media associated with a plurality of cells included in the bioreactor.

13. The bioreactor of claim 1, wherein the liquid additive is inoculant, an acid, a base, a buffering compound, or a nutrient feed.

14. The bioreactor of claim 1, wherein the controller individually controls the at least one the plurality of spargers to generate a horizontal flow of the liquid within the bioreactor.

15. The bioreactor of claim 1, wherein the controller is configured to control the at least one of the plurality of spargers to sparge the liquid at a first rate that is different than sparging rates associated with one or more other spargers of the plurality of spargers.

16. The bioreactor of claim 1, wherein the controller is configured to monitor the pH reading associated with the bioreactor.

17. The bioreactor of claim 16, wherein the reading associated with the bioreactor is determined to be consistent and at the setpoint after monitoring the reading associated with the bioreactor for a particular amount of time.

18. The bioreactor of claim 1, wherein the plurality of vertical circulation loops include corresponding airlift tubes.

19. The bioreactor of claim 1, wherein the first sparging rate is a default sparging rate.

20. The bioreactor of claim 1, further comprising a vessel that includes the plurality of spargers and the plurality of vertical circulation loops.

21. The bioreactor of claim 1, wherein the setpoint associated with the bioreactor is fixed during a cell culture run.

22. The bioreactor of claim 1, wherein the setpoint associated with the bioreactor changes during a cell culture run.

* * * * *